(12) United States Patent
Merandon et al.

(10) Patent No.: US 11,268,955 B2
(45) Date of Patent: Mar. 8, 2022

(54) USE OF ABSORBENT PARTICLES TO IMPROVE SIGNAL DETECTION IN AN ANALYSIS METHOD

(71) Applicant: BIO-RAD EUROPE GMBH, Basel (CH)

(72) Inventors: Bertrand Merandon, Chatillon (FR); Christophe Vedrine, Courbevoie (FR)

(73) Assignee: BIO-RAD EUROPE GMBH, Basel (CH)

( * ) Notice: Subject to any disclaimer, the term of this patent is extended or adjusted under 35 U.S.C. 154(b) by 209 days.

(21) Appl. No.: 15/302,517

(22) PCT Filed: Apr. 8, 2015

(86) PCT No.: PCT/EP2015/057640
§ 371 (c)(1),
(2) Date: Oct. 7, 2016

(87) PCT Pub. No.: WO2015/155255
PCT Pub. Date: Oct. 15, 2015

(65) Prior Publication Data
US 2017/0023566 A1    Jan. 26, 2017

(30) Foreign Application Priority Data
Apr. 9, 2014 (FR) .................................. 1453170

(51) Int. Cl.
*G01N 33/543* (2006.01)
*G01N 33/58* (2006.01)

(52) U.S. Cl.
CPC ..... *G01N 33/54393* (2013.01); *G01N 33/585* (2013.01)

(58) Field of Classification Search
None
See application file for complete search history.

(56) References Cited

U.S. PATENT DOCUMENTS

| 4,318,707 A | 3/1982 | Litman et al. |
| 4,731,337 A | 3/1988 | Luotola et al. |
| (Continued) | | |

FOREIGN PATENT DOCUMENTS

| JP | A-S61-041966 | 2/1986 |
| JP | A-S61-082165 | 4/1986 |
| (Continued) | | |

OTHER PUBLICATIONS

Dodeigne, C. et al. "Chemiluminescence as diagnostic tool. A Review" *Talanta*, Mar. 6, 2000, pp. 415-439, vol. 51, No. 3.
(Continued)

*Primary Examiner* — Xiaoyun R Xu
(74) *Attorney, Agent, or Firm* — Saliwanchik, Lloyd & Eisenschenk

(57) ABSTRACT

The present invention relates to the use of absorbent particles to improve the detection of a signal corresponding to the presence of an analyte in an analysis method on spot(s), in particular when the signal detection takes place in the presence of a liquid phase. The present invention also relates to an analysis method on spot(s) making it possible to improve the detection of a signal corresponding to the presence of an analyte, in the presence of a liquid phase comprising absorbent particles.

15 Claims, 5 Drawing Sheets

(56) References Cited

U.S. PATENT DOCUMENTS

Figure 1:
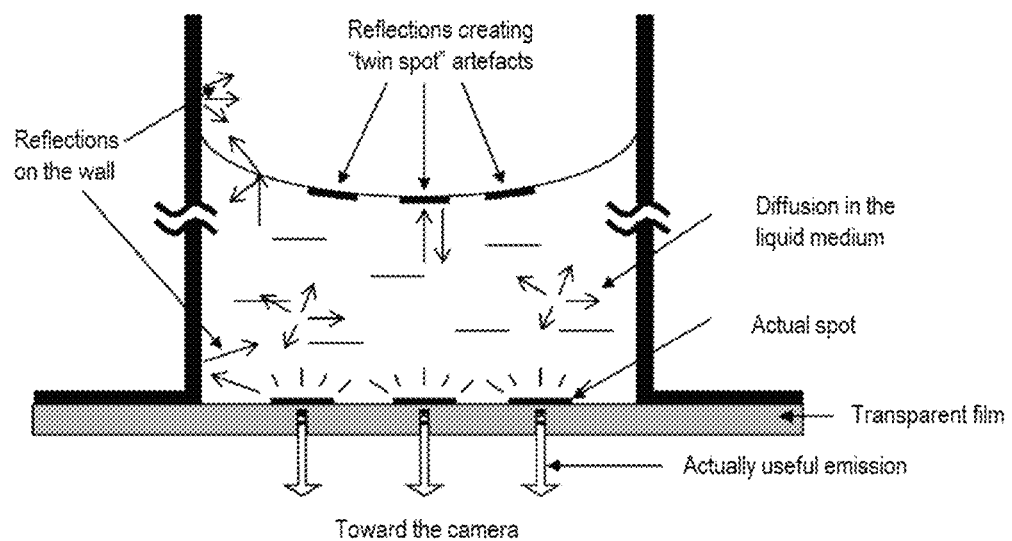

| | | |
|---|---|---|
| 5,082,768 A | 1/1992 | Burd et al. |
| 5,811,312 A | 9/1998 | Hasegawa et al. |
| 5,922,551 A * | 7/1999 | Durbin ............. G01N 33/54346 435/13 |
| 7,700,373 B2 | 4/2010 | McBride et al. |
| 2002/0022274 A1 | 2/2002 | Krahn et al. |
| 2007/0184494 A1 | 8/2007 | McBride et al. |

FOREIGN PATENT DOCUMENTS

| | | | |
|---|---|---|---|
| JP | A-H07-120397 | 5/1995 | |
| JP | H10-318929 | 12/1998 | |
| JP | 2000-512746 | 9/2000 | |
| JP | 2007-505326 | 3/2007 | |
| JP | 2007-535669 | 12/2007 | |
| JP | 2009-186220 | 8/2009 | |
| WO | WO 91/15425 * | 10/1991 | ............. C01B 31/00 |
| WO | WO 2005/106482 | 11/2005 | |
| WO | WO 2015/150583 | 10/2015 | |
| WO | WO 2015/155248 | 10/2015 | |
| WO | WO 2015/155254 | 10/2015 | |

OTHER PUBLICATIONS

Gao, H. et al. "Amorphous carbon nanoparticle used as novel resonance energy transfer acceptor for chemiluminescent immunoassay of transferrin" *Analytica Chimica Acta*, Mar. 28, 2014, pp. 102-107, vol. 819.

Linares, E. M. et al. "Enhancement of the detection limit for lateral flow immunoassays: Evaluation and comparison of bioconjugates" *Journal of Immunological Methods*, Jan. 31, 2012, pp. 264-270, vol. 375, No. 1.

Written Opinion in International Application No. PCT/EP2015/057640, dated May 22, 2015, pp. 1-6.

\* cited by examiner

USE OF ABSORBENT PARTICLES TO IMPROVE SIGNAL DETECTION IN AN ANALYSIS METHOD

CROSS-REFERENCE TO RELATED APPLICATION

This application is the U.S. national stage application of International Patent Application No. PCT/EP2015/057640, filed Apr. 8, 2015.

TECHNICAL FIELD

The present invention relates to the improvement of the detection of a signal corresponding to the presence of an analyte during an analysis method, in particular when the analysis method requires acquiring the signal in the presence of a liquid phase.

BACKGROUND OF THE INVENTION

An analysis method makes it possible to detect the potential presence of one or several analytes in a specimen. An analysis method is generally done on a solid support. Among the analysis methods, the multiplex analysis method allows the simultaneous detection of the potential presence of several analytes within a same specimen. A multiplex analysis method can be done on a solid support comprising spots or a set of beads.

Traditionally, an analysis method comprises a step for placing a specimen to be analyzed in the presence of at least one spot of a solid support or beads comprising a specific capture ligand of an analyte to be detected, a step for adding a specific detection ligand of an analyte to be detected and coupled to a direct or indirect marker, a potential developing step by adding a reporter in turn coupled to a direct or indirect marker, and a signal detection step (also called signal acquisition step). In the case of an indirect marker of a peroxidase enzyme type, the addition of a substrate of the enzyme allows an enzymatic reaction that leads to the production of a chemiluminescent compound. The signal is then detected by chemiluminescence.

The detection of a signal by chemiluminescence requires, in principle, acquiring the signal in the presence of the substrate of the enzyme, i.e., in the presence of a liquid phase, in order to allow the production of the chemiluminescent compound continuously. Indeed, if a wash step is done before acquiring the signal, the residual substrate is eliminated and the enzymatic reaction stops. Yet the signal emitted by the chemiluminescent compound is extinguished gradually. Consequently, the substrate of the enzyme must be present in a liquid phase in contact with the solid phase to allow a stable and reproducible enough signal emission.

However, the acquisition of a signal at the spots of a well of a microplate in the presence of a liquid phase leads to light interference. This light interference has several sources: on the one hand, photons emitted from spots toward the top of the well can interact with the compounds of the solution comprising the chemiluminescent compound and be diffused in all directions; on the other hand, the photons can also be reflected by the walls of the well and by the change in the medium at the liquid/air interface, more specifically at the meniscus formed by the interaction of the wall of the well and the solution comprising the chemiluminescent compound.

This light interference can produce spots called "twin spots", slightly shifted relative to the real spots, a light ring visible on the periphery of the well, or even a light arc when the signal emitted at a spot is strong. This light interference therefore causes problematic background noise, which may be at the source of false negative or false positive results. For example, the light ring around the well can bias the threshold of the background noise, a weak signal then being drowned in the background noise. The light interference can also hinder the verification of the absence of flaws of a spot done by an annular measurement around a spot.

Document U.S. Pat. No. 4,318,707 describes a method for detecting an analyte in a specimen comprising placing the specimen in the presence of an absorbent particle coupled to a first member of a ligand/anti-ligand pair and a second marked member, the quantity of the second marked member bonded to the first member coupled to the absorbent particle is connected to the quantity of analyte. In this document, the absorbent particles are therefore bonded to a first member of the ligand/anti-ligand pair and make it possible to extinguish the signal of the second marked member of said pair, when the two members of the pair are bonded.

Document U.S. Pat. No. 8,163,562 describes a test making it possible to reduce the unwanted light resulting from the fluorescence of a solution in which a cellular compartment bathes that is preferably a cell. This unwanted fluorescence in particular comes from probes or chemical compounds used during the test. The signal to be detected comes from a photon-producing agent situated in the membrane compartment. To that end, a photon-reducing agent impermeable to the membrane and not specifically bonding to the membrane is used in the aqueous solution in contact with the outer surface of the membrane compartment.

There is therefore a need for solutions making it possible to improve the detection of a signal corresponding to the presence of an analyte in the context of an analysis method on spot(s) during which the acquisition of the signal at the spot(s) takes place in the presence of a liquid phase, in order to secure the results obtained while avoiding false positive or false negative results.

DETAILED DESCRIPTION OF THE INVENTION

Surprisingly, in a spot analysis method, the inventors have shown that the use of absorbent particles, for example carbon particles, makes it possible to eliminate some or all of the unwanted light interference ordinarily occurring upon acquisition of a signal in the presence of a liquid phase, but without interfering, or interfering little, with the intensity of the detected signal corresponding to the presence of an analyte at a spot (for example, in luminescence), and making it possible to detect, if applicable, the fluorescence emitted by a fluorophore present as a control at the spot(s). The use of absorbent particles according to the invention thus makes it possible to secure the results obtained at the end of an analysis method, i.e., to guarantee the reliability of said results obtained at the end of said method, in particular by avoiding yielding falsely positive results (also called "false positives") and/or falsely negative results (also called "false negatives").

A "false positive" is a positive result reflecting the presence of one or several analytes to be detected in a specimen, whereas said analyte(s) were not present in the specimen and therefore should not have been detected.

A "false negative" is a negative result reflecting the absence of one or several analytes to be detected in a specimen, whereas said analyte(s) were present in the specimen and should have been detected.

The detected signal corresponding to the presence of an analyte at a spot makes it possible to detect the presence of an analyte in a specimen and/or to quantify said analyte in said specimen.

The detected signal corresponding to the presence of an analyte at a spot is an electromagnetic radiation, in particular a light emission.

The detected signal corresponding to the presence of an analyte at a spot is preferably a signal detected by luminescence, for example by chemiluminescence, and/or a signal detected by fluorescence.

The absorbent particles according to the invention make it possible to improve the detected signal to background noise ratio, when the detected signal corresponding to the presence of an analyte at a spot is a signal detected by luminescence, preferably by chemiluminescence.

A fluorophore present in the spot(s) of a solid support may serve, inter alia, to control the quality of the spot(s) (in particular their presence, location and/or integrity) at the end of an analysis method and/or to improve the sensitivity of the detection of the analyte(s) by defining a reading grid of the signal corresponding to the analyte(s) from the actual location of the spot(s) at the end of the analysis method. The use of a fluorophore in the spot(s) of a solid support therefore also makes it possible to secure the results of a spot analysis method.

Furthermore, the absorbent particles according to the invention make it possible to control the placement of said absorbent particles in the presence of the spot(s) of a compartment of a solid support and, when said absorbent particles are added in the form of an absorbent composition, make it possible to control the placement of any compound comprised in said absorbent composition in the presence of the spot(s) of a compartment of a solid support.

The use of absorbent particles according to the invention thus makes it possible to improve (and therefore secure) the detection of a signal corresponding to the presence of an analyte during an analysis method, by concealing and/or absorbing, partially or fully, the unwanted light interference during the acquisition of a signal to be detected in the presence of a liquid phase. The improvement of the signal detection can be assessed by measuring the "detected signal to background noise" ratio.

Furthermore, the use of absorbent particles in an analysis method according to the invention has the advantage of being able to use a solid support whereof the wall(s) of the compartment(s) comprise or are made up of a transparent material, this type of support being less expensive than those comprising or being made up of an opaque material.

A first object of the invention is to provide an absorbent composition able to be used in an analysis method on spot(s) to improve the detection of a signal corresponding to the presence of an analyte.

A second object of the invention is to provide an analysis method, preferably a multiplex analysis method, making it possible to improve the detection of a signal corresponding to the presence of an analyte comprising the following steps:
a) providing a solid support comprising at least one compartment, said compartment comprising at least one spot intended for the detection of an analyte,
b) placing a specimen to be analyzed in the presence of the spot(s) of said compartment of the solid support,
c) placing at least one detection ligand of an analyte in the presence of the spot(s) of said compartment, said detection ligand of an analyte being coupled to a direct or indirect detection marker,
d) when said detection marker is an indirect detection marker, placing a reporter of the indirect detection marker coupled to said detection ligand in the presence of the spot(s) of said compartment,
e) when the reporter used in step d) is coupled to an indirect marker, placing a reporter of the indirect detection marker coupled to said reporter in the presence of the spot(s) of said compartment,
f) placing absorbent particles in the presence of the spot(s) of said compartment, said absorbent particles being comprised in a liquid phase in contact with the spot(s) of said compartment, and
g) detecting a signal corresponding to the presence of an analyte at the spot(s) of said compartment, in the presence of the liquid phase comprising said absorbent particles.

A third object of the invention relates to the use of absorbent particles to improve the detection of a signal corresponding to the presence of an analyte in an analysis method on spot(s), the improvement in the detection of the signal for example being characterized by a decrease in the intensity of the background noise.

A fourth object of the invention relates to a kit for carrying out an analysis method making it possible to improve the detection of a signal corresponding to the presence of an analyte.

Specimen

The specimen to be analyzed is preferably a biological specimen.

The biological specimen may be a biological fluid, such as a specimen of blood, blood derivatives (such as plasma or serum), urine, cerebrospinal fluid, saliva, or a tissue specimen, such as a tissue obtained by biopsy, a cell, a set of cells, a plant extract, or combinations thereof.

A blood derivative refers to any product, in particular fluid, obtained from a blood sample.

The specimen to be analyzed may also be a culture medium and/or a culture supernatant.

Before being analyzed, the specimen may undergo one or several prior treatment steps, such as dilution, centrifugation, heat treatment, cell lysis (for example by one or several chaotropic agents, one or several reducing agents and/or by heating), extraction, PCR (Polymerase Chain Reaction), addition of an unmarked detection ligand or combinations thereof. The addition of an unmarked detection ligand is in particular useful to implement a neutralization test, which in itself is a test known by those skilled in the art.

The specimen may also be a mixture of at least two specimens that may be of the same nature or different natures.

Examples of mixtures of specimens of different natures are a mixture of blood and serum, a mixture of blood and plasma, a mixture of serum and plasma, or a mixture of blood, serum and plasma.

One preferred specimen according to the invention is a specimen or mixture of specimens of blood and/or blood derivatives.

Analyte

An analyte to be detected in a specimen may be any type of compound, natural or synthetic, that one wishes to detect and/or quantify in a specimen.

An analyte may for example be a protein, a peptide, a glycoprotein, a carbohydrate, a lipid, a cell, an organelle, a virus or a nucleic acid.

The cell may be an animal cell, a plant cell, a bacteria cell, a protozoa, a metazoan cell, a yeast cell, or a fungus cell.

A nucleic acid designates a polymer of nucleotides linked by phosphodiester bonds, such as a deoxyribonucleic acid (DNA), a ribonucleic acid (RNA) or an analogue thereof, such as phosphorothioates or thioesters, in single-strand or double-stranded form.

An analyte or at least one of the analytes is for example chosen from the group consisting of an antigen, an antibody, an antibody fragment, a hapten, a hormone, a hormone receptor, an enzyme, or a nucleic acid.

"Antigen" here refers to a natural or synthetic molecule recognized by antibodies or cells of the immune system and capable of inducing an immune response. An antigen is for example a protein, a peptide, a glycoprotein, a carbohydrate or a lipid.

"Hapten" here refers to a molecule with a low molecular weight capable of being recognized by the immune system, but which is immunogenic only when it is coupled to a carrier molecule.

In the present application, a "carrier molecule" in particular refers to a protein or carbohydrate carrier molecule. A carrier molecule may be a polypeptide (in particular protein or a peptide), which may or may not be natural (for example, a recombinant protein or a synthetic peptide), a functionalized polymer (such as dextran, polysaccharide or polylysine), a mixed copolymer (in particular a copolymer of different amino acids, for example a lysine-tyrosine copolymer) or an antibody (in particular a monoclonal antibody or a polyclonal antibody), for example an immunoglobulin (also called Ig). One example of a carrier molecule is BSA (bovine serum albumin).

An analyte or at least one of the analytes is preferably a compound making it possible to diagnose a condition in a subject, which may or may not be pathological, or to diagnose the risk of developing a condition, which may or may not be pathological. An example of a non-pathological condition is a pregnancy.

The subject may be a human, a non-human animal or a plant. The non-human animal is preferably a mammal, such as a cat, dog, monkey, rabbit, mouse or rat.

The term "human" is used broadly and in particular designates a man or a woman of any age, such as an infant, a child, an adolescent, an adult or an elderly person.

When the analyte or at least one of the analytes is an antigen, it is preferably an antigen making it possible to diagnose an infection, for example an infection caused by a virus, a bacteria, a fungus or a parasite.

When the analyte or at least one of the analytes is an antibody, it is preferably an antibody making it possible to diagnose an infection, for example an infection caused by a virus, a bacteria, a fungus or a parasite.

Typically, this may involve one or several antigens and/or one or several antibodies of:
  a virus, such as HIV (Human Immunodeficiency Virus), in particular HIV-1 or HIV-2, HBV (Hepatitis B Virus), HCV (Hepatitis C Virus), HPV (Human Papilloma Virus), HTLV (Human T-Lymphotropic Virus), in particular HTLV-I or HTLV-II,
  a parasite, such as a parasite that may cause toxoplasmosis (in particular *Toxoplasma gondii*), malaria (in particular a parasite of the *Plasmodium* genus, for example *Plasmodium falciparum, Plasmodium vivax, Plasmodium ovale, Plasmodium malariae* or *Plasmodium knowlesi*) or Chagas disease (in particular *Trypanosoma cruzi*) in humans or non-human animals, or
  a bacteria, such as a bacteria able to cause syphilis (*Treponema pallidum*) or Lyme disease (in particular a bacteria from the *Borrelia* genus) in humans or non-human animals.

"Parasite" here refers to a metazoan or a protozoa acting as parasite with respect to a body and causing parasitosis. A parasite within the meaning of the invention is therefore not a virus, a bacteria or a fungus.

The analyte or at least one of the analytes may also be a marker for disease, such as a marker of a cardiovascular disease or a diabetes marker, a marker of the evolution of the disease, such as hepatitis, a marker of the evolution of an infection caused by a virus, a bacteria, a fungus, a parasite, or a marker of resistance to a treatment, for example an antiviral treatment, an antibiotic treatment or a cancer treatment.

Several (for example, two, three, four, five, six, seven, eight, nine, ten, eleven, twelve, thirteen, fourteen, fifteen, sixteen or more than sixteen) analytes as described in the present application may be detected simultaneously in a specimen during a multiplex analysis method. This may make it possible to diagnose, in a same specimen, one or several infections or diseases, the evolution of an infection or disease, a condition (pathological or not), a risk of developing a condition (pathological or not) or a marker of resistance to a treatment in a subject.

The analytes detected during a multiplex analysis method may be of the same nature (for example only antibodies or only antigens) or of different natures (for example, at least one antigen and at least one antibody).

Capture Ligand

A capture ligand is a compound fixed on a solid support at a spot.

At least one capture ligand is specific to an analyte to be detected in the specimen.

A capture ligand may be an antibody, an antigen, a peptide, a carbohydrate, a lipid or a nucleic acid.

A capture ligand is preferably an antibody or an antigen.

When a capture ligand is an antibody, for example, it involves a monoclonal antibody or a polyclonal antibody.

Detection Ligand

A detection ligand is intended to reveal the presence of a compound to which it is specific.

A detection ligand may be an antibody, an antigen, a peptide, a carbohydrate, a lipid or a nucleic acid.

A detection ligand is preferably an antibody or an antigen.

When a detection ligand is an antibody, for example, it involves a monoclonal antibody or a polyclonal antibody.

A detection ligand is preferably a marked detection ligand, i.e., a detection ligand to which a detection marker is attached, covalently or non-covalently.

When a detection ligand is not marked, its detection may be obtained by using a specific marked antibody of said detection ligand.

At least one detection ligand is specific to an analyte to be detected in the specimen.

A detection ligand may be identical to the used capture ligand or one of the used capture ligands, with the exception of any presence of a detection marker, and/or bind to the compound to which it is specific at the same zone as that bonded by the capture ligand or one of the capture ligands. In this case, if said capture ligand and said detection ligand are antibodies, it then involves an "allogenic sandwich".

A capture ligand and the detection ligand or one of the detection ligands can be specific to separate zones at the compound to which they are specific, so as to avoid competition of the capture ligand and the detection ligand with respect to the compound to which they are specific, due to a steric hindrance. In this case, if said detection ligand and said capture ligand are antibodies, it then involves an "allogenic sandwich".

In one preferred embodiment, a detection ligand and a capture ligand specific to a same compound do not bond to the same location on said compound. More preferably, said detection ligand bonds to a zone of said compound that is far from the binding zone with said capture ligand.

In another preferred embodiment, a detection ligand is identical to a capture ligand, with the exception of any presence of a detection marker, and/or bonds to the compound to which it is specific at the same zone as that bonded by said capture ligand, in particular when the compound to which it is specific is in the form of a complex having at least two identical bonding zones.

Detection Marker

A detection marker may be a direct marker or an indirect marker.

A direct marker is a marker whose signal can be detected directly, i.e., without requiring the prior addition of a reporter.

A direct marker is for example selected from the group consisting of a fluorophore, a luminescent compound, and fluorescent or luminescent nanoparticles.

A "luminescent" compound may be an electroluminescent compound, a thermoluminescent compound or a chemiluminescent compound. In one preferred embodiment, the luminescent compound is a chemiluminescent compound.

One example of a luminescent compound (more specifically, a thermoluminescent compound) that may be used as a direct marker consists of silica nanoparticles comprising (for example doped with) molecules of a dioxetane compound, in particular the 1,2-dioxetane compound, or a derivative of a dioxetane compound, for example a derivative of 1,2-dioxetane.

An indirect marker is a marker for which detection of the signal requires the prior addition of a reporter (also called first reporter) and, if said reporter itself is coupled to an indirect detection marker (for example, an enzyme), the addition of a second reporter of the indirect detection marker coupled to said first reporter (for example, a substrate of this enzyme).

An indirect marker is for example selected from the group consisting of an enzyme, a ligand of a ligand-receptor pair, a receptor of a ligand-receptor pair, a hapten, an antigen and an antibody.

A ligand or a receptor of a ligand-receptor pair is for example biotin, an analogue of biotin, avidin, streptavidin, neutravidin or digoxigenin.

A reporter is a substrate of an indirect marker or a molecule specifically bonding to an indirect marker, said molecule itself being a direct or indirect marker or itself being coupled to a direct or indirect marker.

A substrate is for example the substrate of an enzyme.

A molecule specifically bonding to an indirect marker is, for example, a ligand or a receptor of a ligand-receptor pair, such as biotin, an analogue of biotin, avidin, streptavidin, neutravidin or digoxigenin.

A reporter of an enzyme is for example a substrate of said enzyme.

A reporter of a molecule making it possible to produce a luminescent compound is for example a substrate, an enzyme or a catalyst.

A reporter of the biotin is, for example, avidin, streptavidin or neutravidin, preferably coupled with a direct marker or an indirect marker, such as an enzyme.

Preferred indirect markers according to the invention are biotin and an enzyme, preferably an enzyme producing a luminescent compound by reaction with a substrate.

An example of an enzyme is peroxidase, for example horseradish peroxidase (HRP), a luciferase or an alkaline phosphatase.

One preferred biotin reporter according to the invention is streptavidin coupled with a peroxidase, preferably horseradish peroxidase.

As an example, if the reporter (called first reporter) of the indirect detection marker coupled to a detection ligand of an analyte is coupled to a peroxidase enzyme, it is necessary to add, in a subsequent step, the reporter (also called second reporter) of this peroxidase enzyme, i.e., a substrate of this enzyme, such as luminol, isoluminol and/or a derivative of luminol or isoluminol. In this case, the second reporter is a substrate.

Solid Support

The support(s) used to carry out an analysis method according to the invention are solid supports.

A solid support can be made from any material appropriate to carry out an analysis method.

A solid support is for example a support with a base of a polymer or a mixture of polymers. An appropriate solid support according to the invention is for example a support made from polystyrene, polypropylene, poly(meth)acrylate, polybutadiene or combinations thereof.

One preferred solid support is made from polystyrene and/or polypropylene.

Another type of appropriate solid support according to the invention is for example an inorganic solid support, such as glass.

The support may for example be in the form of a plate, a microplate, a slide or a membrane.

A solid support comprises at least one compartment, which is also called analysis zone. The compartment(s) of a solid support define the orientation of a solid support. The top of a solid support (also called upper face of said solid support) is located on the side of the compartment(s) and therefore on the side of the spot(s). The bottom of a solid support (also called lower face of a solid support) is the opposite face.

According to one particular embodiment of the invention, a solid support comprises a single compartment. Said single compartment may be a compartment comprising or made up of a bottom and one or several walls.

Alternatively, said single compartment can have no walls and then be comparable to the solid support itself. The bottom of the compartment can then consist of the upper face of said solid support.

One example of such a solid support comprising a single compartment (that may or may not comprise one or several walls) is a slide or a membrane.

According to another particular embodiment of the invention, a solid support, which may for example be a microplate, comprises at least two compartments.

When a solid support comprises at least two compartments, they are isolated from one another, such that they do not communicate with one another, i.e., such that the various compositions (in particular solutions) used during the implementation of an analysis method cannot circulate from one compartment to another during the analysis method.

Thus, a solution added into one compartment will not go into the other compartments. For example, the compartment(s) comprise or are made up of a bottom and one or several walls, said wall(s) isolating the compartment(s) from one another such that they do not communicate with one another.

A solid support is preferably a microplate. In this case, one example of a compartment is a well. The microplate is typically a microplate with 96 wells or 384 wells.

In one particular embodiment, when a solid support comprises at least two compartments, they can further be isolated from one another, such that the signal emitted at one compartment is not, in whole or in part, detected in another compartment. To that end, the wall(s) of the compartment(s) may comprise or be made up of an opaque material.

"Opaque material" in particular refers to a material not or substantially not allowing the signal to be detected corresponding to the presence of an analyte to pass. "Substantially not allowing the signal to be detected to pass" means that the opaque material allows no more than 20%, preferably no more than 15%, more preferably no more than 10%, still more preferably no more than 5%, and even more preferably no more than 2%, no more than 1% or no more than 0.5% of the signal to be detected to pass. One example of an opaque material is a black material.

In another particular embodiment, when a solid support comprises at least two compartments, the wall(s) of the compartment(s) comprise or are made up of a transparent material.

In another particular embodiment, when a solid support comprises at least two compartments, the compartment(s) can comprise at least one wall made up of a transparent material and at least one wall made up of an opaque material.

"Transparent material" in particular refers to a material allowing at least 80% of a signal to be detected corresponding to the presence of an analyte to pass, preferably at least 85% of the signal to be detected, more preferably at least 90% of the signal to be detected, more preferably at least 95% of the signal to be detected.

In one preferred embodiment, the bottom of the compartment(s) of a solid support comprises or is made up of a transparent material, so as to allow the detection of the signal to be detected corresponding to the presence of an analyte through the bottom of the compartment.

Examples of opaque materials are colored glass, colored polystyrene, colored polyethylene, colored polypropylene or combinations thereof.

Examples of transparent materials are glass, polystyrene, polymethylpentene, polycarbonate, acrylonitrile butadiene styrene, polymethyl methacrylate or combinations thereof.

Typically, at least one (for example one or two) compartment of a solid support is used per specimen to be analyzed.

In one particular embodiment of the invention where a solid support (for example a slide or a membrane) comprises a single compartment, at least one (for example one or two) solid support is used per specimen to be analyzed.

A compartment of a solid support used to analyze a specimen comprises at least one spot, at least two spots, at least three spots, for example three spots, four spots or five spots, or at least six spots, preferably six spots, seven spots, eight spots, more preferably at least nine spots, for example nine spots, ten spots, eleven spots, twelve spots, thirteen spots, fourteen spots, fifteen spots, sixteen spots or more than sixteen spots.

"Spot" here refers to a zone situated on the surface of the bottom on a compartment of a solid support comprising at least one compound of interest. The compound(s) of interest can thus be fixed to the surface of the bottom of a compartment, through noncovalent physicochemical interactions (for example of the weak bond type, and in particular ionic, van der Waals, hydrogen and/or hydrophobic) and/or by covalent bonds.

A spot may comprise, aside from the compound(s) of interest, at least one polymer, in particular at least one polymer including hydrophilic groups, for example at least one hydrogel.

"At least", within the meaning of the present application, refers to one or several, several in particular meaning two, three, four, five, six, seven, eight, nine, ten, eleven, twelve, thirteen, fourteen, fifteen, sixteen or more than sixteen.

A spot corresponds to a well-defined zone, generally small, for example comprised between 0.0078 $mm^2$ and 5.309 $mm^2$, preferably from 0.196 $mm^2$ to 3.142 $mm^2$, more preferably comprised from 0.503 $mm^2$ to 2.011 $mm^2$.

A spot may have a discoid or approximately discoid shape, for example oval, in particular when a solid support is a microplate or a slide.

Alternatively, a spot may have a square or rectangular shape (in particular a strip), for example when a solid support is a membrane, or any other shape.

The spots are obtained using techniques well known by those skilled in the art (see for example documents U.S. Pat. Nos. 7,470,547, 6,576,295, 5,916,524 or U.S. Pat. No. 5,743,960).

For example, a spot is obtained by depositing at least one drop of a solution containing a determined quantity of said compound(s) of interest in a specific location on the surface of the compartment.

When a spot comprises at least one polymer (for example at least one hydrogel), said spot may be obtained by depositing at least one drop of a solution containing a determined quantity of said compound(s) of interest in a specific location on the surface of the compartment on which said polymer has been previously deposited.

A spot can also be obtained by in situ synthesis of said compound(s) of interest in a specific location on the surface of the compartment. Said compound(s) of interest are qualified as probes in this case. This may involve a nucleic acid or a peptide (see for example document U.S. Pat. No. 5,143,854).

The compound of interest may for example be a capture ligand, a carrier molecule coupled to an indirect marker, an indirect marker or a fluorophore.

In one preferred embodiment, at least one spot of a compartment comprises at least one capture ligand specific to an analyte to be detected.

In one advantageous embodiment, at least one spot of a compartment, preferably all of the spots of a compartment, comprises at least two compounds of interest, one of these compounds of interest being a fluorophore. Said fluorophore is in particular used to control the presence, location and/or integrity of the spots at the end of an analysis method, in particular a multiplex analysis method. For example, at least one spot of a compartment comprises at least one detection ligand specific to an analyte and at least one fluorophore.

In one advantageous embodiment, each compartment of a solid support comprises the same number of spots. Furthermore, each compartment of a solid support comprises the same number of spots and the same spot composition.

In another advantageous embodiment, the support may comprise one or several compartments without spots, or with a different number of spots and/or spot composition. The support may for example comprise at least two separate groups (or types) of compartments, each of the separate groups having a different number of spots and/or spot composition.

A compartment generally comprises at least one spot per analyte to be detected, each analyte for example being able to correspond to an infection or disease to be detected, the evolution of an infection or disease, a condition (pathological or not) of the subject, a risk of developing a condition (pathological or not) or a marker of resistance to a treatment. Several spots of a compartment may also be intended to analyze a same analyte. A compartment therefore comprises at least one spot intended for the detection of an analyte, preferably at least two spots intended to detect an analyte.

A same spot may comprise several different capture ligands (for example, several antibodies and/or antigens), which are for example specific to a same pathology, infection or disease to be detected (in particular specific to a same virus, a same bacteria, a same fungus or a same parasite), or specific to a same evolution of an infection or disease, a same condition (pathological or not) of a subject, a same risk of developing a condition (pathological or not) or a same marker of resistance to a treatment.

In one advantageous embodiment, a compartment comprises at least one control spot, making it possible to validate at least one step of an analysis method, in particular, a multiplex analysis method.

Detection of the Signal

The detection of the signal depends on the type of marker used.

The detected signal is an electromagnetic radiation.

The electromagnetic radiation may be light, for example ultraviolet radiation, visible light or infrared radiation. Ultraviolet radiation is an electromagnetic radiation having a wavelength from 10 to 380 nm. Visible light is an electromagnetic radiation with a wavelength comprised from 380 nm to 780 nm. Infrared radiation is an electromagnetic radiation with a wavelength comprised from 780 nm to 1 mm.

The expressions "detection of the signal" and "acquisition of the signal" are synonymous here.

"Detection of the signal" in particular refers to the detection of a signal corresponding to the presence of an analyte or the detection of a signal corresponding to a control of the method.

One skilled in the art knows how to detect a signal at a spot based on the detection marker(s) used. The signal is for example detected using a camera that captures the image of the bottom of the solid support.

The detection of the signal generally comprises measuring the intensity of the signal, for example expressed in RLU (Relative Light Unit).

The signal emitted by a direct marker of the fluorophore type can be read directly by fluorescence, after excitation by light energy.

Indeed, a fluorophore, also called fluorochrome or fluorescent molecule, is a clinical substance capable of emitting fluorescent light after excitation with a light energy.

In the context of the present invention, the absorbent particles used must be present during the detection of the signal and the detection of the signal is done in the presence of a liquid phase.

By using absorbent particles according to the invention, it is possible to decrease the background noise and in particular to improve the "detected signal to background noise" ratio, by detecting the signal corresponding to the presence of an analyte emitted at the spots, said signal preferably being detected by capturing an image of the bottom of the solid support.

In one preferred embodiment, the signal detected in the analysis method according to the invention is a signal emitted by chemiluminescence by a chemiluminescent compound.

Chemiluminescence is a chemical reaction resulting in the production of light. One reaction of this type is the oxidation-reduction of luminol (3-aminophthalhydrazide, also called 5-amino-2,3-dihydro-phthalazine-1,4-dione, with raw formula $C_8H_7N_3O_2$), isoluminol and/or a derivative of the luminol or the isoluminol by an oxidizer, for example oxygenated water or any hydroxide. During a chemiluminescence reaction, the molecule produced by the reaction is found in an excited state; this is the chemiluminescent compound. It is the return of this chemiluminescent compound to the fundamental state that causes the emission of light.

In one preferred embodiment, the signal detected by chemiluminescence is emitted by the reaction of a peroxidase enzyme with its substrate, for example luminol, isoluminol (also called 4-aminophthalhydrazide) and/or a derivative of the luminol or isoluminol. This reaction also requires the presence of an oxidizer and, if applicable, an electron mediator.

A derivative of luminol or isoluminol is preferably a molecule obtained from the luminol or the isoluminol, respectively, through all possible modification(s) (for example, chemical and/or enzymatic). A derivative of luminol or isoluminol is for example a substrate of a peroxidase enzyme, the reaction of said peroxidase enzyme with said derivative of the luminol or the isoluminol making it possible to produce a chemiluminescent compound.

A derivative of the isoluminol may for example be aminoethylisoluminol (or AEI), aminoethylethylisoluminol (or AEEI), aminobutylisoluminol (or ABI), aminobutylethylisoluminol (or ABEI), aminopentylethylisoluminol (or APEI), aminohexylisoluminol (or AHI), aminohexylethylisoluminol (or AHEI), aminooctylmethylisoluminol (or AOMI) or aminooctylethylisoluminol (or AOEI), as described in Dodeigne C. et al. (2000), Talanta 51, 415-439, "Chemiluminescence as diagnostic tool. A review".

According to another particular embodiment of the invention, the signal detected by chemiluminescence is emitted via an enzymatic or chemical reaction with a substrate chosen from among an acridine, coelenterazine, dioxetane or peroxyoxalic compound, or one of their derivatives, and in particular a compound described in Dodeigne C. et al. (2000), Talanta 51, 415-439, "Chemiluminescence as diagnostic tool. A review".

An electron mediator is, for example, sodium 3-(10'phenothiazinyl)propane 1-sulfonate, p-iodophenol, p-iodophenylboronic acid, 4-(phenothiazine-10-yl)butane-1-sulfonic acid, or combinations thereof.

An oxidizer is for example a peroxide, for example a hydrogen peroxide, or sodium perborate.

The signal resulting from the reaction of a peroxidase enzyme with the luminol, isoluminol and/or a derivative of the luminol or isoluminol is read at a wavelength comprised from 375 nm to 580 nm, for example 425 nm.

The detected signal is preferably expressed in RLU (Relative Light Unit). The peroxidase enzyme may be coupled with a detection ligand, for example a specific detection ligand of an analyte, or with a reporter of an indirect detection marker, such as streptavidin.

Generally, the chemiluminescence reaction is done using a kit comprising at least two solutions.

The first solution comprises the substrate for the peroxidase, for example the luminol, the isoluminol and/or a derivative of the luminol or the isoluminol, and an electron mediator; the second solution comprises an oxidizer. As an example, it is possible to use the following kits: "Immun-star western C" (Bio-Rad, United States), "ELISTAR ETA C Ultra ELISA" (Cyanagen, Italy), "Supersignal West Pico" (Thermo Scientific, United States), and "Chemiluminescent Sensitive Plus HRP" (Surmodics, United States).

Fluorophore Used as Control

In one advantageous embodiment, the spot(s) of at least one compartment of a solid support comprise a fluorophore used as control.

The fluorophore used as control preferably does not interfere or interferes very little with the signal corresponding to the presence of an analyte, for example with the signal emitted by a chemiluminescent compound.

As an example, when the signal corresponding to the presence of an analyte is a chemiluminescent compound obtained from the luminol, the isoluminol and/or a derivative of the luminol or the isoluminol, the fluorophore used as control preferably does not emit light around 425 nm, in particular 400 nm to 550 nm, preferably from 375 nm to 550 nm, more preferably from 350 nm to 580 nm. It may for example emit light only at wavelengths less than (or less than or equal to) 400 nm, 390 nm, 380 nm, 375 nm, 370 nm, 360 nm or 350 nm, or only at wavelengths greater than (or greater than or equal to) 550 nm, 560 nm, 570 nm, 580 nm, 590 nm or 600 nm.

A fluorophore used as control is, for example, selected from the group consisting of a coumarin, a rhodamine, a carbopyronine, an oxazine, benzopyrylium, a phycoerythrin and derivatives thereof. Said fluorophore is optionally coupled to a carrier molecule, for example a protein such as BSA.

A fluorophore used as control is, for example, selected from the group consisting of a coumarin, a rhodamine, a carbopyronine, an oxazine, B-phycoerythrin, a derivative of benzopyrylium, and derivatives thereof.

One fluorophore used as control is, preferably, selected from the group consisting of a carbopyronine, a derivative of a carbopyronine, an oxazine, an oxazine derivative, a benzopyrylium derivative, and a phycoerythrin.

One still more preferred fluorophore for use as a control is selected from the group consisting of a carbopyronine, a benzopyrylium derivative, and a phycoerythrin.

Alternatively, one preferred fluorophore for use as a control may be selected from the group consisting of a carbopyronine derivative, a benzopyrylium derivative, and a phycoerythrin.

One preferred fluorophore that may be used in the spots as a control is for example a carbopyronine comprising the following basic structure:

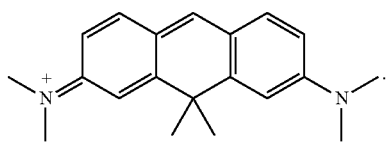

Examples include the Atto 633 carbopyronine marketed by Atto-Tec and its derivatives, in particular an amine derivative of Atto 633.

Another example of a preferred fluorophore that may be used in the spots as a control is the fluorophore marketed by Dyomics under the name "Dye 634" (in its form coupled to a carrier molecule, for example BSA), the formula for which is as follows:

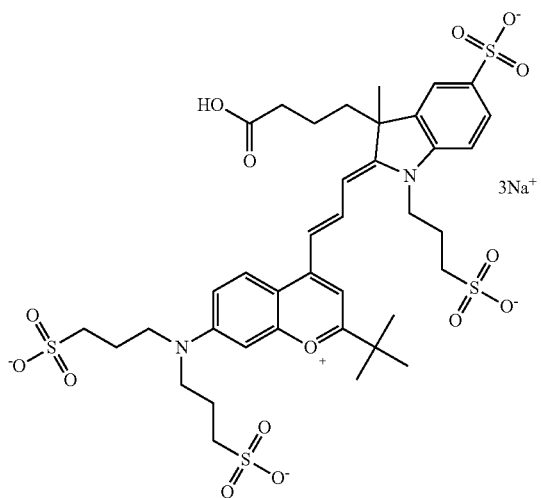

This is a benzopyrylium derivative.

The Dye 634 fluorophore can also be used in its amine form (Dye 634-amine) in the spots as a control. It may then be used coupled or not coupled to a carrier molecule, and in particular BSA.

Still another example of a preferred fluorophore derived from benzopyrylium that may be used in the spots as a control is the amine derivative of Dye 630, Dye 630 having the following formula:

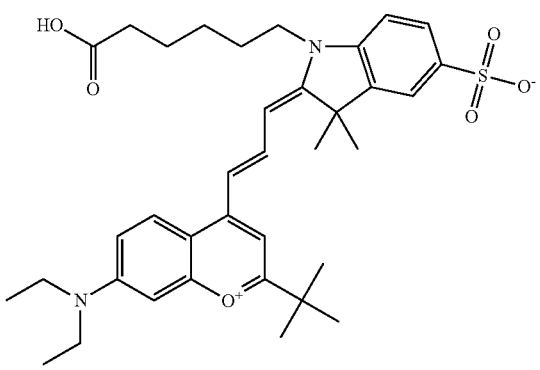 [SMILES: CCN(CC)c1ccc2c(/C=C/C=C3/N(CCCCCC(=O)O)c4ccc(S(=O)(=O)[O-])cc4C3(C)C)cc(C(C)(C)C)[o+]c2c1]

The amine derivative of Dye 630 may be used coupled or not coupled to a carrier molecule, and in particular BSA.

Absorbent Particles

"Absorbent particles" here refers particles that absorb the light in a wavelength range partially or completely overlapping the emission wavelength range of the signal that one seeks to reduce (partially or fully), i.e., the signal at the origin of the light interference.

When a luminescent compound, for example a chemiluminescent compound, is used in an analysis method to detect the presence of an analyte, absorbent particles according to the invention preferably absorb the light in a wavelength range completely overlapping the emission wavelength range of said luminescent compound.

Typically, for a developing system using the reaction of a peroxidase on the luminol, the isoluminol and/or a derivative of the luminol or the isoluminol, the absorbent particles according to the invention preferably absorb a wavelength range comprised from 375 nm to 580 nm.

When a fluorophore is used in an analysis method to detect the presence of an analyte in a specimen, and optionally, to quantify an analyte in a specimen, the absorbent particles used make it possible to detect the signal emitted by said fluorophore. Thus, the absorbent particles used can absorb all or part of the light at wavelengths comprised in the excitation and/or emission wavelength range of said fluorophore, as long as the signal emitted by said fluorophore remains detectable and/or quantifiable in the analysis method used. Furthermore, preferably, the absorbent particles do not diffuse light corresponding to the excitation and/or emission wavelength range of said fluorophore.

In one particular embodiment, when a fluorophore is used in an analysis method to detect the presence of an analyte in a specimen and/or to quantify an analyte in a specimen, the absorbent particles used do not absorb light in a wavelength range corresponding to the excitation and/or emission wavelength range of said fluorophore, and preferably do not diffuse light corresponding to the excitation and/or emission wavelength range of said fluorophore.

In one preferred embodiment, the potential diffusion caused by the absorbent particles does not hinder an increase in the signal level of the bottom of the well, in particular by absorbing more light than they diffuse. The absorbance and diffusion are measurable using techniques known by those skilled in the art.

In one preferred embodiment, the absorbent particles are not fluorescent in the red, i.e., they do not emit light at wavelengths comprised from 620 to 780 nm when they are excited by any light, in particular in a basic medium.

In one particular embodiment, absorbent particles according to the invention do not absorb at 657 nm, in particular do not absorb between 620 and 780 nm, between 610 and 800 nm, between 600 and 900 nm or between 580 and 950 nm, and themselves are not fluorescent.

Preferably, the absorbent particles used in the context of the present invention are not fluorescent.

Surprisingly, the absorbent particles according to the invention absorb the signal at the origin of the light interferences, without interfering or interfering little with the signal to be detected, for example not interfering or interfering little with the light emitted by the chemiluminescent compound resulting from the reaction of a peroxidase enzyme with the luminol, the isoluminol and/or a derivative of the luminol or the isoluminol locally at the spots.

The expression "the compound X does not interfere or interferes little with a signal" here means that the intensity of the signal in the presence of the compound X is decreased by no more than 20%, preferably no more than 15%, still more preferably no more than 10%, relative to the intensity measured in the absence of said compound X.

Furthermore, the absorbent particles according to the invention do not cause an energy transfer with the chemiluminescent compound, as can be observed with fluorescein, which can enter an activated state and emit at a wavelength higher than the emission wavelength of the chemiluminescent compound produced by the reaction of a peroxidase enzyme with its substrate (for example the luminol, isoluminol and/or a derivative of luminol or isoluminol).

The absorbent particles preferably have a diameter smaller than 50 µm, preferably smaller than 40 µm, for example smaller than 30 µm or smaller than 20 µm, more preferably smaller than 10 µm, more preferably smaller than 6 µm, more preferably smaller than 2 µm, more preferably smaller than 1 µm, still more preferably smaller than 0.5 µm. For example, the absorbent particles have a diameter smaller than 0.45 µm.

The average diameter of the absorbent particles is preferably comprised from 0.005 µm to 50 µm, 0.005 µm to 40 µm, 0.005 µm to 30 µm, 0.005 µm to 20 µm, 0.005 µm to 10 µm, 0.005 µm to 6 µm, or 0.01 µm to 2 µm, preferably 0.01 µm to 1 µm, more preferably 0.05 µm to 0.5 µm, still more preferably from 0.05 µm to 0.1 µm. The average diameter of the absorbent particles is for example 0.050 µm or 0.070 µm.

The expressions "diameter of the particles" and "size of the particles" are synonymous here.

The diameter of the absorbent particles can be measured by any appropriate method well known by those skilled in the art, for example using a particle analyzer, for example of the Nanotrac NPA150 type.

"Average diameter" here refers to the average of the diameters of the absorbent particles, each diameter being defined by the diameter of the equivalent sphere having the same volume as the considered absorbent particle.

In one advantageous embodiment, the absorbent particles according to the invention further make it possible to detect the signal emitted by a fluorophore present as control in the spot(s). Such absorbent particles are for example obtained or able to be obtained using the absorbent particle selection method as defined below in the paragraph "method for selecting absorbent particles further allowing the detection of the signal emitted by a fluorophore present in the spot(s) as a control".

The absorbent particles according to the invention are for example selected in the group consisting of carbon particles and color particles.

The absorbent particles according to the invention may be made up of a mixture of different (at least two) types (or groups) of particles, said types of particles differing by their absorption spectrum and/or their average diameter.

Thus, the color particles can for example be contributed in the form of a mixture of color particles, preferably a mixture of different color particles, the absorption spectrum of said mixture of color particles preferably completely overlapping the emission wavelength range of the signal corresponding to the analyte to be detected (for example the signal of the luminol, the isoluminol and/or one of their derivatives). Two or more than two (for example, three) types of particles of different colors can be mixed.

Preferably, the color particles used in the mixture of color particles do not comprise black particles.

The absorbent particles according to the invention are for example a mixture of yellow particles and magenta particles.

The particles contributed in the form of a mixture may be chosen such that said mixture absorbs all of the visible light.

The carbon particles are preferably carbon black particles.

Carbon black is an amorphous and elementary form of carbon.

The yellow particles are for example contributed in the form of a composition comprising butanamide, 2-[2-(2-methoxy-4-nitrophenyl)diazenyl]-N-(2-methoxyphenyl)-3-oxo-, a derivative of mono(4-sulfophenyl) and a sodium salt.

The magenta particles are for example contributed in the form of a composition comprising water, benzenesulfonic acid, (5,7,12,14-tetrahydro-2,9-dimethyl-7,14-dioxoquino[2,3-b]acridinyl) and a sodium salt.

The mixture of magenta particles and yellow particles for example comprises the yellow and magenta particles in a 1:1 weight ratio.

Thus, surprisingly, the absorbent particles according to the invention make it possible to partially or completely reduce the light interference coming from a chemiluminescent compound, without interfering, or interfering little, with the signal to be detected by chemiluminescence and, if applicable, with the fluorescence emitted by a fluorophore present in the spots as a control.

Advantageously, the presence of absorbent particles according to the invention is visible to the naked eye (in particular appearing as a disc with a homogenous brightness darker or lighter than the material of the solid support), which thus makes it possible to control the placement of the absorbent particles in the presence of the spot(s) of a compartment of a solid support and, when said absorbent particles are added in the form of an absorbent composition, to control the placement of any compound comprised in said absorbent composition in the presence of the spot(s) of a compartment of a solid support.

One skilled in the art can easily determine the optimal quantity of absorbent particles to be used in a multiplex analysis method on spots to obtain the desired improved detection of the signal, for example by testing several concentrations of said absorbent particles.

In one preferred embodiment, the absorbent particles are carbon particles, in particular carbon black particles.

The carbon particles used in the context of the present invention preferably have a diameter smaller than 50 µm, preferably smaller than 40 µm, smaller than 30 µm or smaller than 20 µm, more preferably smaller than 10 µm or smaller than 6 µm. According to one particular embodiment, said carbon particles have a diameter smaller than 2 µm, preferably smaller than 1 µm, more preferably smaller than 0.5 µm. For example, the carbon particles used in the context of the present invention have a diameter smaller than 0.45 µm.

The average diameter of the carbon particles used in the context of the present invention is preferably comprised from 0.005 µm to 50 µm, 0.005 µm to 40 µm, 0.005 µm to 30 µm, 0.005 µm to 20 µm, 0.005 µm to 10 µm or 0.005 µm to 6 µm. According to one particular embodiment, the average diameter of said carbon particles is comprised from 0.005 µm to 2 µm, preferably from 0.01 µm to 1 µm, more preferably from 0.05 µm to 0.5 µm, still more preferably from 0.05 µm to 0.1 µm. The average diameter of the carbon particles is for example 0.05 µm or 0.07 µm.

The carbon particles can be obtained using any method well known by those skilled in the art, for example as described in documents U.S. Pat. No. 7,655,209 or EP 0,481,034.

In one advantageous embodiment, functional groups are attached to the surface of the carbon particles. These functional groups for example make it possible to obtain a stable and homogenous dispersion, without using polymer or surfactant. The functional groups able to be used are for example those described in document EP 0,481,034.

Method for Selecting Absorbent Particles Further Allowing the Detection of the Signal Emitted by a Fluorophore Present in the Spot(s) as a Control The present invention also relates to a method for selecting absorbent particles further allowing the detection of the signal emitted by a fluorophore present in the spot(s) of a solid support, said method comprising the following steps:

a) placing a liquid phase comprising absorbent particles to be tested or a mixture of absorbent particles to be tested in contact with the spot(s) of a compartment of a solid support, at least one of the spots of said compartment comprising a fluorophore, b) detecting a signal emitted by said fluorophore in the presence of said liquid phase comprising said absorbent particles to be tested or said mixture of absorbent particles to be tested, and c) selecting absorbent particles or a mixture of absorbent particles in the presence of which the signal detected in step b) makes it possible to localize the spot(s) comprising said fluorophore.

The absorbent particles to be tested or comprised in the mixture to be tested are particles that absorb the light in a wavelength range partially or completely overlapping the emission wavelength range of the signal that one seeks to reduce (partially or fully), i.e., the signal at the origin of the light interference.

Step a) is carried out for each of the absorbent particles or each of the mixtures of absorbent particles to be tested.

In step a), absorbent particles to be tested or a mixture of absorbent particles to be tested can be added in several compartments, for example at different concentrations, in order to test different concentrations of said absorbent particles or of said mixture of absorbent particles.

A different compartment is used for each of the absorbent particles to be tested or each of the different mixtures of absorbent particles to be tested.

Absorbent composition with a base of absorbent particles

In one preferred embodiment, the absorbent particles as defined above in the "absorbent particles" paragraph are contributed in the form of an absorbent composition.

The present invention therefore also relates to an absorbent composition comprising absorbent particles as defined above making it possible to improve (and thus secure) the detection of the signal of a multiplex analysis method on spots.

Here, an absorbent composition comprising absorbent particles according to the invention is called a dispersion.

A "dispersion" designates a mixture of solid particles in a liquid, said solid particles having an average diameter comprised from 0.005 µm to 50 µm, 0.005 µm to 40 µm, 0.005 µm to 30 µm, 0.005 µm to 20 µm, 0.005 µm to 10 µm, 0.005 µm to 6 µm, or 0.01 µm to 2 µm, preferably 0.01 µm to 1 µm.

The absorbent composition according to the invention may comprise from 1% to 80% of absorbent particles, preferably from 2% to 60% of absorbent particles, more preferably from 5% to 50% of absorbent particles, more preferably from 7% to 40% of absorbent particles, still more preferably from 10% to 30% of absorbent particles, the percentages being expressed by weight of the total weight of the absorbent composition. For example, the absorbent composition may comprise from 10% to 20% of absorbent particles, more preferably from 12% to 18% of absorbent particles, the percentages being expressed by weight of the total weight of the absorbent composition. For example, the absorbent composition comprises 15% of absorbent particles, the percentage being expressed by weight of the total weight of the absorbent composition.

In one advantageous embodiment, the absorbent composition comprises absorbent particles and at least one compound selected from the group consisting of a vehicle, a binder and an additive.

The vehicle used in the absorbent composition may be a solvent, for example water.

The solvent used in the absorbent composition may for example be methyl ethyl ketone (MEK), an acetate, a glycol ether, an alcohol or combinations thereof.

The binder in particular makes it possible to adjust the viscosity of the absorbent composition.

Examples of binders are a phenolic resin and/or a copolymer.

The additive is for example a biocide and/or an antifoaming agent.

One preferred absorbent composition according to the invention comprises or consists of absorbent particles, water, optionally a sodium salt and optionally a biocide, said absorbent particles being able to be coupled to one or several functional groups. One still more preferred absorbent composition according to the invention comprises or consists of carbon particles (preferably carbon black particles), water, optionally a sodium salt and optionally a biocide, said carbon particles being able to be coupled to one or several functional groups, for example 4-carboxypheynl-, hydroxy- and/or 4-sulfophenyl-groups.

Advantageously, the absorbent particles settle little in the absorbent composition, so as to have a homogeneous dispersion of the particles that remains stable over time, without requiring mixing said composition.

The absorbent composition preferably has a relatively low viscosity, so that it can be pipetted easily.

The absorbent composition preferably has a viscosity comprised from 0.5 cP to 3 cP, more preferably from 1 cP to 2.5 cP. The absorbent composition for example has a viscosity of 2.1 cP.

The viscosity can be measured via any appropriate method well known by those skilled in the art, for example using a rotation viscosimeter, for example of the Brookfield type.

The pH of the absorbent composition is preferably comprised from 7 to 12, preferably from 8 to 10, for example 9.7.

The surface tension is preferably comprised from 60 dynes/cm to 80 dynes/cm, preferably from 65 dynes/cm to 75 dynes/cm, for example 70 dynes/cm.

The surface tension can be measured via any appropriate method well known by those skilled in the art, for example using a tensiometer of the Kruss type.

In one advantageous embodiment, the absorbent composition does not comprise a polymer or surfactant.

The absorbent composition may comprise or consist of the CAB-O-JET® 352K product, the CAB-O-JET® 400 product, the CAB-O-JET® 200 product by Cabot (United States), the Aquablak® 5109 product, the Aquablak® 6152 product, the Aquablak® 6353 product by Solution Dispersions (United States) or combinations thereof.

The absorbent composition can also comprise or consist of a mixture of yellow absorbent particles contributed in the form of the CAB-O-JET® 270 product by Cabot (United States) and magenta absorbent particles contributed in the form of the CAB-O-JET® 260M product by Cabot (United States).

The absorbent composition may comprise one or several, or all, of the features described above.

One preferred absorbent composition according to the invention has at least one of the following features, preferably at least two, at least three or at least four, for example at least five, at least six, or all of the following features:
  it comprises absorbent particles having a diameter smaller than 0.5 µm, for example smaller than 0.45 µm,
  it comprises absorbent particles having an average diameter comprised from 0.06 µm to 0.1 µm, for example an average diameter of 0.070 µm,
  it comprises absorbent particles on the surface of which functional groups are attached,
  it comprises from 12% to 18% of absorbent particles, for example 15% of absorbent particles, the percentages being expressed by weight of the total weight of the absorbent composition.
  it has a surface tension comprised from 65 dynes/cm to 75 dynes/cm, for example 70 dynes/cm,
  it has a pH comprised from 8 to 10, for example 9.5, and/or
  it has a viscosity comprised from 1 cP to 2.5 cP, for example a viscosity of 2.1 cP.

The absorbent composition according to the invention may also be diluted before use, in particular in water or any other solvent compatible with the detection of the signal used and in particular compatible with an enzymatic reaction leading to the production of a luminescent compound, for example a solvent as described in the present application. For example, the absorbent composition according to the invention may be diluted 10 to 2000 times, preferably 100 to 1000 times, for example 100 times, 200 times, 500 times or 1000 times.

The absorbent composition can also comprise or consist of a mixture of yellow particles and magenta particles, as previously described.

Advantageously, the absorbent composition comprises absorbent particles and at least one compound involved in the production of a luminescent compound, in particular a chemiluminescent compound.

One preferred absorbent composition according to the invention thus comprises or consists of absorbent particles, at least one compound involved in the production of a chemiluminescent compound, water, optionally a sodium salt and optionally a biocide, said absorbent particles being possibly coupled to one or several functional groups. One still more preferred absorbent composition according to the invention comprises or consists of carbon particles (preferably carbon black particles), at least one compound involved in the production of a chemiluminescent compound, water, optionally a sodium salt and optionally a biocide, said carbon particles being possibly coupled to one or several functional groups, for example 4-carboxypheynl-, hydroxy- and/or 4-sulfophenyl-groups.

Surprisingly, such compositions with a base of absorbent particles and at least one compound involved in the production of a chemiluminescent compound are stable over time.

The expression "stable over time" means that, during the implementation of a same analysis method, the signal detected using an absorbent composition on DO is substantially identical to the signal detected by using said absorbent composition after keeping said absorbent composition for at least one month at 4° C. and/or 37° C., preferably for at least 3 months at 4° C., for example 3 months, 6 months, one year or two year at 4° C.

The expression "substantially identical" means that the detected signal varies by no more than 40%, preferably no more than 30%, more preferably no more than 20%.

The absorbent composition can thus be mixed with one or several compositions and/or one or several compounds used in the context of an analysis method, in particular used during the developing step(s).

In one advantageous embodiment, the absorbent composition according to the invention further comprises at least one compound selected from the group consisting of the luminol, the isoluminol, a derivative of the luminol or the isoluminol, an electron mediator and an oxidizer.

The luminol, the isoluminol, the derivative of the luminol or the isoluminol, the peroxidase enzyme, the electron mediator and the oxidizer are in particular as defined above.

One preferred absorbent composition comprises absorbent particles, for example particles of carbon, at least one compound selected from among the luminol, the isoluminol, a derivative of the luminol or the isoluminol and, optionally, an electron mediator.

Another preferred absorbent composition comprises absorbent particles, for example particles of carbon, and at least one oxidizer, for example a peroxide.

The absorbent compositions according to the invention advantageously comprise at least one solvent.

A solvent used in the absorbent composition is preferably compatible with an enzymatic reaction leading to the production of a luminescent compound, such as the reaction of the peroxidase with the luminol, the isoluminol and/or a derivative of the luminol or the isoluminol.

One preferred solvent able to be used in the absorbent composition is water.

Another example of a preferred absorbent composition comprises absorbent particles, for example particles of carbon, and does not comprise luminol, isoluminol, derivative of the luminol or the isoluminol, electron mediator or oxidant. For example, such an absorbent composition comprises or consists of carbon particles and a solvent, for example water.

Kit for Implementing an Analysis Method on Spot(s)

The present invention also relates to a kit for implementing an analysis method, in particular using a solid support comprising at least one spot, said kit comprising at least two compositions:
- a first composition comprising at least one compound selected from the group consisting of the luminol, the isoluminol, and a derivative of the luminol or the isoluminol, and optionally comprising at least one electron mediator, and
- a second composition comprising at least one compound selected from the group consisting of an oxidizer and an electron mediator, said second composition preferably comprising at least one oxidizer, and optionally at least one electron mediator, characterized in that the first composition and/or the second composition comprises absorbent particles and/or in that said kit comprises a third composition comprising absorbent particles.

The absorbent particles and the solid support are in particular as defined above.

The present invention in particular relates to a kit for implementing an analysis method, in particular using a solid support comprising at least one spot, said kit comprising:
- a first absorbent composition comprising absorbent particles and at least one compound selected from the group consisting of the luminol, the isoluminol, and a derivative of the luminol or the isoluminol, and optionally comprising at least one electron mediator, and
- a second composition comprising at least one compound selected from the group consisting of an oxidizer and an electron mediator, said second composition preferably comprising at least one oxidizer, and optionally at least one electron mediator.

The present invention in particular relates to a kit for implementing an analysis method, in particular using a solid support comprising at least one spot, said kit comprising:
- a first composition comprising at least one compound selected from the group consisting of the luminol, the isoluminol, and a derivative of the luminol or the isoluminol, and optionally comprising at least one electron mediator, and
- a second absorbent composition comprising absorbent particles and at least one compound selected from the group consisting of an oxidizer and an electron mediator, said second absorbent composition preferably comprising at least one oxidizer, and optionally at least one electron mediator.

The present invention in particular relates to a kit for implementing an analysis method, in particular using a solid support comprising at least one spot, said kit comprising:
- a first composition comprising at least one compound selected from the group consisting of the luminol, the isoluminol, and a derivative of the luminol or the isoluminol, and optionally comprising at least one electron mediator,
- a second composition comprising at least one compound selected from the group consisting of an oxidizer and an electron mediator, said second composition preferably comprising at least one oxidizer, and optionally at least one electron mediator, and
- a third absorbent composition comprising absorbent particles.

The analysis method is advantageously a multiplex analysis method.

Improvement of the Detection of the Signal

The use of absorbent particles as defined above or of an absorbent composition comprising them as defined above makes it possible to improve (and thus secure) the detection of the signal in an analysis method on spot(s), preferably a multiplex analysis method on spots, in particular when the detection of the signal is done in the presence of a liquid phase.

"Improve the detection of the signal" in particular means decreasing the background noise, and more particularly improving the "detected signal to background noise" ratio, in the presence of absorbent particles or of the absorbent composition comprising them, relative to the "detected signal to background noise" ratio obtained in their absence.

The "detected signal" to assess the improvement of the "detected signal to background noise" ratio is for example the intensity of the signal measured at a given spot (i.e., in the location where said spot is found) in the presence of an analyte to be detected in a specimen or measured at a given spot (i.e., in the location where said spot is located) in the presence of a known quantity of an analyte to be detected.

Preferably, the "detected signal" to assess the improvement of the "detected signal to background noise" ratio is the intensity of the signal measured at a given spot (i.e., in the location where said spot is found) in the presence of an analyte present in a quantity that induces, in the absence of absorbent particles, light interference, such as a light arc and/or a twin spot and/or a light web.

The intensity of the signal measured at a spot is generally expressed in RLU (Relative Light Unit).

One skilled in the art knows how to detect a signal at a spot (i.e., at the location where said spot is found) based on the detection marker(s) used, in particular using a camera that is advantageously situated below the solid support.

The "background noise" is the light intensity measured at the zones of the background of a compartment of a solid support that do not comprise spots.

The background noise is generally expressed in RLU (Relative Light Unit).

An improvement in the "detected signal to background noise" ratio is present when the "detected signal to background noise" ratio is increased, for example by increasing the detected signal and decreasing the background noise, or by decreasing the detected signal and still further decreasing the background noise.

The use of absorbent particles according to the invention makes it possible, preferably, to increase the "detected signal to background noise" ratio, in the presence of absorbent particles versus in the absence of absorbent particles, by at least 5%, preferably at least 10%, more preferably at least 15%, more preferably at least 20%, still more preferably at least 25%, for example at least 30%, or at least 40%.

The present invention is particularly suitable for an analysis method on spot(s), in particular a multiplex analysis method on spots, based on a chemiluminescent developing. Indeed, in order for the signal emitted by chemiluminescence to allow a detection of the capture ligand-analyte-detection ligand interaction by amplifying the signal, it is necessary for the enzymatic reaction to continue during the detection of the signal, and therefore for the substrate of the enzyme to be present in a liquid phase at the spots, at the time of detection of the signal.

In the context of the present invention, the absorbent particles, for example contributed in the form of an absorbent composition, must be present at the time of detection of the signal.

The absorbent particles can be added before, at the same time as or after the addition of one or several of the compounds necessary for the chemiluminescence reaction. In all cases, the absorbent particles must be present at the time of acquisition of the signal.

The compounds necessary for a chemiluminescence reaction are generally an enzyme (for example, a peroxidase enzyme), a substrate of the enzyme (for example, luminol, isoluminol and/or a derivative of luminol or isoluminol), optionally at least one other compound such as an oxidizer (for example, a peroxide) and/or an electron mediator (for example, sodium 3-(10'phenothiazine)propane 1-sulfonate).

Method for Improving the Detection of the Signal

The present invention particularly relates to an analysis method, in particular a multiplex analysis method, making it possible to improve (and thus secure) the detection of a signal corresponding to the presence of an analyte, said method comprising or consisting of the following steps:
  a) providing a solid support comprising at least one compartment, said compartment comprising at least one spot intended for the detection of an analyte,
  b) placing a specimen to be analyzed in the presence of the spot(s) of said compartment,
  c) placing at least one detection ligand of an analyte in the presence of the spot(s) of said compartment, said detection ligand of an analyte being coupled to a direct or indirect detection marker,
  d) when said detection marker is an indirect detection marker, placing a reporter of the indirect detection marker coupled to said detection ligand in the presence of the spot(s) of said compartment,
  e) when the reporter used in step d) is coupled to an indirect marker, placing a reporter of the indirect detection marker coupled to said reporter in the presence of the spot(s) of said compartment,
  f) placing absorbent particles in the presence of the spot(s) of said compartment, said absorbent particles being comprised in a liquid phase in contact with the spot(s) of said compartment, and
  g) detecting a signal corresponding to the presence of an analyte at the spot(s) of said compartment, in the presence of a liquid phase comprising said absorbent particles.

The method according to the invention preferably first comprises step a); then steps b) and c), which can be done in that order, or step c) before step b), or steps b) and c) at the same time; then step d); then steps e) and f), which can be done in that order, or step f) before step e), or steps e) and f) at the same time; then step g).

In one preferred embodiment, step f) is carried out at the same time as step e).

No wash step is done between step f) and step g) (whether step e) is done before, after, or at the same time as step f)), such that the absorbent particles are present at the time of detection of the signal.

When step c) is done before step b), there is no wash step between steps c) and b).

The expression "place a compound X in the presence of one or several spots of a compartment" in particular means that the compound X is added into a compartment comprising said spot(s), said compartment preferably being intended to analyze a specimen, and said compound X preferably being contributed in the form of a composition comprising it, such as a solution, a dispersion or a suspension.

When at least two compounds are to be placed in the presence of the spot(s) of the compartment during a same step and/or when at least two steps b) to f) are done at the same time, said compounds may be placed in the presence of said spot(s) separately, i.e., contributed in the form of separate compositions (in particular in the form of separate solutions, dispersions or suspensions); alternatively, said compounds or some of the compounds may be placed in the presence of the spot(s) of a compartment in the form of one or several mixtures.

Different compounds are placed in the presence of spots of at least one compartment for a certain length of time, for example from 1 second to 2 hours, preferably 1 minute to 1 hour, more preferably 5 minutes to 50 minutes, still more preferably from 10 minutes to 40 minutes.

One skilled in the art knows how to determine the appropriate temperature for each incubation step. The temperature of an incubation may for example be 4° C., a temperature comprised from 19° C. to 24° C., 37° C. or 40° C.

The different components used during steps b), c), d) and e) are well known by those skilled in the art. They for example make it possible to form antigen-antibody and marker-reporter complexes.

The method further comprises one or several wash steps that make it possible to eliminate the compounds not bonded to the spots or to the various compounds directly or indirectly bonded to the spots.

Typically, a wash step consists of at least one cycle, preferably at least two cycles, more preferably 3 to 6 cycles, for distributing (for example, a volume of 400 µl) and aspirating a wash solution in each compartment used.

Steps b) to g) are in particular done for each compartment of a solid support comprising at least one spot intended to detect an analyte, in which a specimen is analyzed.

Step a) consists of providing a solid support comprising at least one compartment, said compartment comprising at least one spot intended for the detection of an analyte, preferably at least two spots intended to detect an analyte.

Step a) in particular means that the analysis method is implemented using said solid support, i.e., using said solid support.

The solid support is in particular as defined above in the "solid support" paragraph.

In one advantageous embodiment, the solid support comprises at least one compartment whereof at least one spot comprises a fluorophore as control for the spot(s); preferably, the solid support comprises at least one compartment whereof the spots comprise a fluorophore as control for the spots.

In step b), a specimen to be analyzed is placed in the presence of the spot(s) of a compartment of the solid support.

The specimen to be analyzed and the analyte(s) to be detected are in particular as defined above in the "specimen" and "analyte" paragraphs.

In step c), at least one detection ligand of an analyte is placed in the presence of the spot(s) of said compartment, said detection ligand of an analyte being coupled to a direct or indirect detection marker.

The detection ligand of an analyte is in particular as defined above.

In one preferred embodiment, a detection ligand of an analyte is coupled to an indirect detection marker, preferably selected from the group consisting of biotin, avidin, streptavidin and neutravidin.

When the detection marker is an indirect detection marker, the method comprises a step d) comprising or consisting of placing a reporter (also called first reporter) of the indirect detection marker coupled to said detection ligand in the presence of the spot(s) of said compartment, said reporter in turn being coupled to a direct or indirect marker, preferably an indirect marker.

In one preferred embodiment, a reporter of the indirect detection marker coupled to a detection ligand of an analyte is selected from the group consisting of biotin, avidin, streptavidin and neutravidin.

For example, a detection ligand of an analyte is coupled to the biotin and the reporter of the biotin is streptavidin coupled to a direct or indirect detection marker, preferably an indirect detection marker.

When the reporter (i.e., the first reporter) used in step d) is coupled to an indirect marker, the method further comprises a step e) consisting of placing a reporter (i.e., a second reporter) of the indirect detection marker coupled to said reporter in the presence of the spot(s) of said compartment.

For example, a detection ligand of an analyte is coupled to the biotin and the reporter of the biotin is streptavidin coupled to an enzyme. The reporter of the enzyme (i.e., the second reporter) is then the substrate of said enzyme.

In step f), absorbent particles are placed in the presence of the spot(s) of said compartment.

The absorbent particles are in particular as defined above in the "absorbent particles" paragraph.

In particular, the absorbent particles are preferably carbon particles, for example particles of carbon black, or a mixture of color particles, for example a mixture of yellow color particles and magenta color particles.

The absorbent particles can be contributed in the form of an absorbent composition as defined above in the "absorbent composition" paragraph.

In one advantageous embodiment, the absorbent particles are contributed in the form of an absorbent composition comprising at least one compound selected from the group consisting of the luminol, the isoluminol, a derivative of the luminol or the isoluminol, an electron mediator and an oxidizer.

When the absorbent composition further comprises at least one compound selected from the group consisting of the luminol, the isoluminol, a derivative of the luminol or the isoluminol, an electron mediator and an oxidizer, steps e) and f) are therefore carried out at the same time.

At the end of step f), the absorbent particles are comprised in a liquid phase in contact with the spot(s) of said compartment.

"Liquid phase in contact with the spot(s) of said compartment" here means that a liquid composition is present in said compartment, said composition for example being able to be a solution, a dispersion or a suspension.

The liquid phase in step f) can comprise or consist of an absorbent composition according to the invention, in particular depending on whether step f) is carried out before step e).

The liquid phase in step f) can comprise or consist of an absorbent composition according to the invention, in particular depending on whether step f) is carried out before step e). When step f) is carried out at the same time as or after step e), the liquid phase in step e) may comprise the absorbent composition.

Step g) comprises detecting a signal corresponding to the presence of an analyte at the spot(s) of said compartment, the detection of said signal being done in the presence of the liquid phase comprising said absorbent particles.

The liquid phase in step g) can be identical to the liquid phase in step f), in particular when step f) is carried out after step e).

The liquid phase in step g) can be different from the liquid phase in step f), in particular when step f) is carried out before step e).

When the absorbent particles are contributed in the form of an absorbent composition, the liquid phase in step g) comprises or consists of said absorbent composition.

When several different detection markers are used in the analysis method to detect the analyte(s), step g) comprises detecting as many different signals as there are detection markers used.

The signal detected in step g) corresponding to the presence of an analyte is for example the signal emitted by a luminescent compound, preferably a chemiluminescent compound, and/or the signal emitted by a fluorophore.

In one preferred embodiment, the signal detected in step g) corresponding to the presence of an analyte is a signal emitted by a luminescent compound, preferably a chemiluminescent compound, and optionally, a signal emitted by a fluorophore.

In one more preferred embodiment, the signal detected in step g) corresponding to the presence of an analyte is not a signal emitted by a fluorophore.

Preferably, the signal detected in step g) corresponding to the presence of an analyte is the signal emitted by a chemiluminescent compound.

Thus, step g) comprises at least detecting a signal emitted at the spot(s) of said compartment that corresponds to the presence of an analyte, the signal corresponding to the presence of an analyte preferably being emitted by a chemiluminescent compound.

In one preferred embodiment, the signal corresponding to the presence of an analyte detected in step g) is therefore emitted by a chemiluminescent compound. In one preferred embodiment, step g) therefore comprises detecting a signal corresponding to the presence of an analyte at the spot(s) of said compartment, by chemiluminescence, in the presence of a liquid phase comprising said absorbent particles.

Furthermore, step g) can advantageously comprise the detection of a signal emitted by a fluorophore present as control in one, several or the spot(s) of at least one compartment of the solid support.

One skilled in the art knows how to measure the emitted signal, for example via a luminescent compound or via a fluorophore, based on the nature of said luminescent compound or said fluorophore.

The signal is preferably detected in step g) through the bottom of the solid support.

The detection of the signal preferably comprises a measurement of the intensity of the signal emitted at the spot(s), said measurement preferably being done through the bottom of the solid support, i.e., at the lower face of the solid support.

The detection of the signal is in particular done using a camera capturing the image of the bottom of the solid support. The measured signal is therefore the signal traversing the solid support toward the lower face of said solid support.

The camera can for example be oriented toward the bottom of the solid support or can capture the image of the bottom of the solid support using an optical system (which may for example comprise or consist of one or several mirrors, a prism and/or one or several lenses).

The measurement of the intensity of the signal emitted by a fluorophore requires lighting the compartment(s), preferably from the bottom of the solid support, with a light corresponding to the excitation spectrum of the fluorophore.

The method according to the invention thus makes it possible to improve the detection of a signal corresponding to the presence of an analyte in an analysis method on spot(s), in particular when the signal detection is done in the presence of a liquid phase.

The improvement of the signal detection comprises or consists of a decrease in the background noise, preferably an increase of the "detected signal to background noise" ratio.

The "detected signal to background noise" ratio is in particular as defined above.

One preferred method making it possible to improve the detection of a signal corresponding to the presence of an analyte in an analysis method, in particular a multiplex analysis method, is a method as defined above comprising the following steps:

a) providing a solid support comprising at least one compartment, said compartment comprising at least one spot intended for the detection of an analyte, said spot comprising a capture ligand of said analyte, and preferably, a fluorophore, b) placing a specimen to be analyzed in the presence of the spot(s) of said compartment, c) placing at least one detection ligand of an analyte in the presence of the spot(s) of said compartment, said detection ligand of an analyte being coupled to an indirect detection marker, preferably biotin, d) placing a reporter of the indirect detection marker coupled to said detection ligand in the presence of the spot(s) of said compartment, preferably streptavidin, e) when the reporter used in step d) is coupled to a peroxidase enzyme, placing a substrate of said enzyme, for example luminol, isoluminol and/or a derivative of luminol or isoluminol, in the presence of the spot(s) of said compartment, e1) when the reporter used in step d) is coupled to a peroxidase enzyme, placing at least one oxidizer, for example peroxide, and optionally at least one electron mediator, for example sodium 3-(10'phenothiazinyl)propane 1-sulfonate, in the presence of the spot(s) of said compartment, said step e1) being able to be done before step e), after step e) or at the same time as step e), f) placing absorbent particles, preferably carbon particles or a mixture of yellow color particles and magenta color particles, in the presence of the spot(s) of said compartment, said absorbent particles being comprised in a liquid phase in contact with the spot(s) of said compartment, step f) being able to be done before or after step e), before or after step e1), or at the same time as step e) and/or step e1), and g) detecting a signal corresponding to the presence of an analyte at the spot(s) of said compartment, in the presence of the liquid phase comprising said absorbent particles.

The method according to the invention can be implemented using a kit as defined above.

Use of Absorbent Particles to Improve Signal Detection

The present invention particularly relates to the use of absorbent particles to improve (and thus secure) the detection of a signal corresponding to the presence of an analyte in an analysis method on a solid support comprising at least one spot, in particular in a multiplex analysis method.

The solid support is in particular as defined above in the "solid support" paragraph.

The solid support in particular comprises at least one compartment, said compartment comprising at least one spot intended for the detection of an analyte, preferably at least two spots intended to detect an analyte.

The absorbent particles are in particular as defined above in the "absorbent particles" paragraph. In particular, the absorbent particles are preferably carbon particles, for example particles of carbon black, or a mixture of color particles, for example a mixture of yellow color particles and magenta color particles.

The present invention in particular relates to the use as defined above, characterized in that the absorbent particles are preferably carbon particles, preferably particles of carbon black, or a mixture of color particles, for example a mixture of yellow color particles and magenta color particles.

The absorbent particles can be contributed in the form of an absorbent composition as defined above in the "absorbent composition" paragraph.

In one more preferred embodiment, the present invention in particular relates to the use of carbon particles, preferably carbon black particles, or a mixture of color particles, preferably a mixture of yellow color particles and magenta color particles, to improve the detection of a signal corresponding to the presence of an analyte in an analysis method on spot(s), in particular in a multiplex analysis method on spot(s).

The present invention more particularly relates to the use as defined above, characterized in that the detection of a signal corresponding to the presence of an analyte is done in the presence of a liquid phase.

The detection of the signal preferably comprises a measurement of the intensity of the signal emitted at the spot(s), said measurement preferably being done at the lower face of the solid support. The detection of the signal is in particular done using a camera capturing the image of the bottom of the solid support.

As indicated above, the camera can for example be oriented toward the bottom of the solid support or can capture the image of the bottom of the solid support using an optical system (which may for example comprise or consist of one or several mirrors, a prism and/or one or several lenses).

The present invention particularly relates to a method as defined above, characterized in that the detected signal to background noise ratio is increased.

The "detected signal to background noise" ratio is in particular as defined above.

The present invention preferably relates to the use as defined above, characterized in that the signal corresponding to the presence of an analyte is a signal emitted by a chemiluminescent compound and/or a fluorophore, preferably by a chemiluminescent compound.

The present invention also relates to the use as defined above, wherein the analysis method is implemented using a solid support as defined above, in particular a solid support comprising at least one compartment whereof at least one spot comprises a fluorophore as control for the spot(s), preferably a solid support comprising at least one compartment whereof the spots comprise a fluorophore as control for the spots.

The present invention also relates the use of absorbent particles to improve (and thus secure) the detection of the signal in a multiplex analysis method on spots as defined above using a kit as defined above.

Other features and advantages of the invention will better emerge through the following examples, provided as an illustration and non-limitingly. These examples and figures illustrate the invention without limiting its scope.

FIGURES

FIG. 1: Diagrammatic cross-section of a well of a microplate. Three actual spots are shown on the bottom of the well, which is made up of a transparent film. The hollow arrows pointing downward show the actually useful emission that departs toward the camera. The solid arrows show the path of the light rays in the well. These arrows illustrate the presence of light artifacts originating from the diffusion of light in the liquid medium, reflections on the wall of the well, at the liquid/air interface and at the meniscus.

Figure 2:
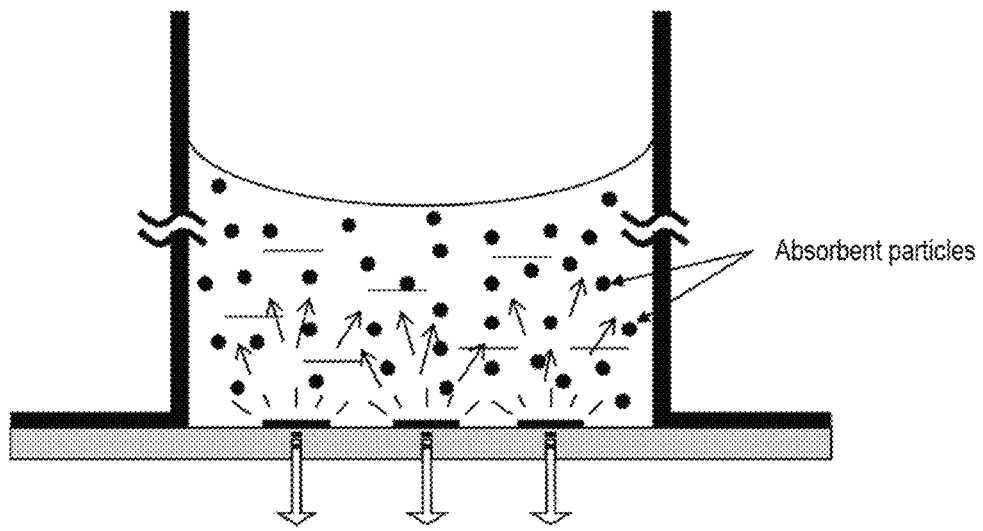

FIG. 2: Diagrammatic cross-section of a well of a microplate. Three actual spots are shown on the bottom of the well, which is made up of a transparent film. The hollow arrows pointing downward show the actually useful emission that departs toward the camera. The solid arrows show the path of the light rays in the well and the intensity of these rays. The black circles show the absorbent particles that make it possible to absorb the light emitted in the liquid medium, thus decreasing the diffusion of light in the liquid medium and the light artifacts at the walls of the well, at the air/liquid interface and at the meniscus.

Figure 3:
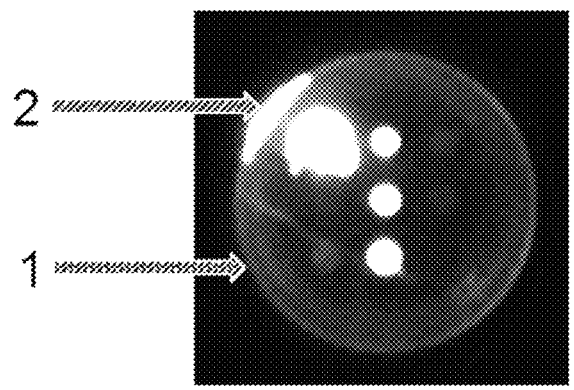

FIG. 3: Image of a well with the specimen 51, without adding the absorbent composition. 1: light ring. 2: light arc.

Figure 4:
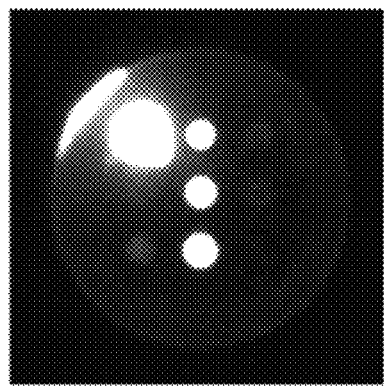

FIG. 4: Image of a well with the specimen 51, with the absorbent composition diluted at 1/1000.

Figure 5:
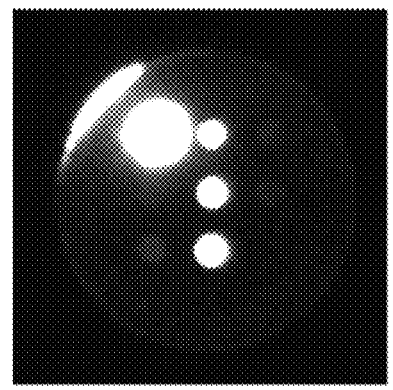

FIG. 5: Image of a well with the specimen 51, with the absorbent composition diluted at 1/500.

Figure 6:
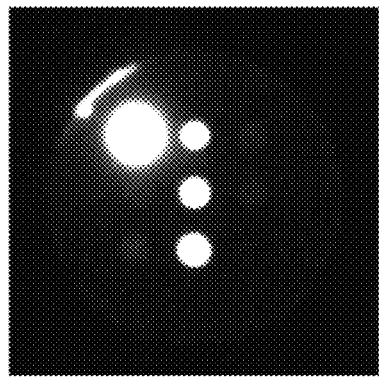

FIG. 6: Image of a well with the specimen 51, with the absorbent composition diluted at 1/200.

Figure 7:
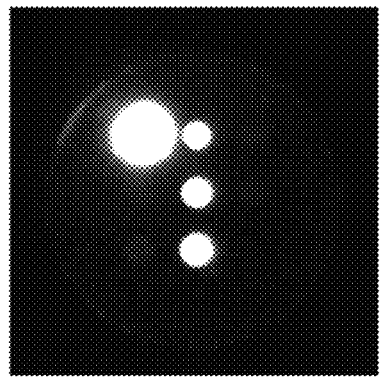

FIG. 7: Image of a well with the specimen 51, with the absorbent composition diluted at 1/100.

Figure 8:
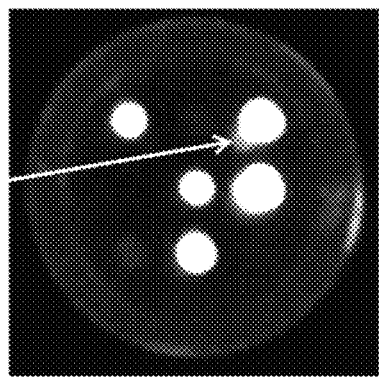

FIG. 8: Image of a well with the specimen S2, without adding the absorbent composition. The arrow indicates a twin spot.

Figure 9:
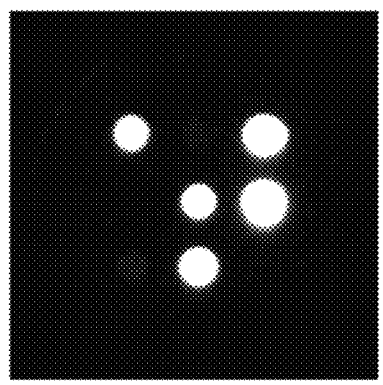

FIG. 9: Image of a well with the specimen S2, under the same conditions as FIG. 8, but in the presence of the absorbent composition diluted at 1/200.

Figure 10:
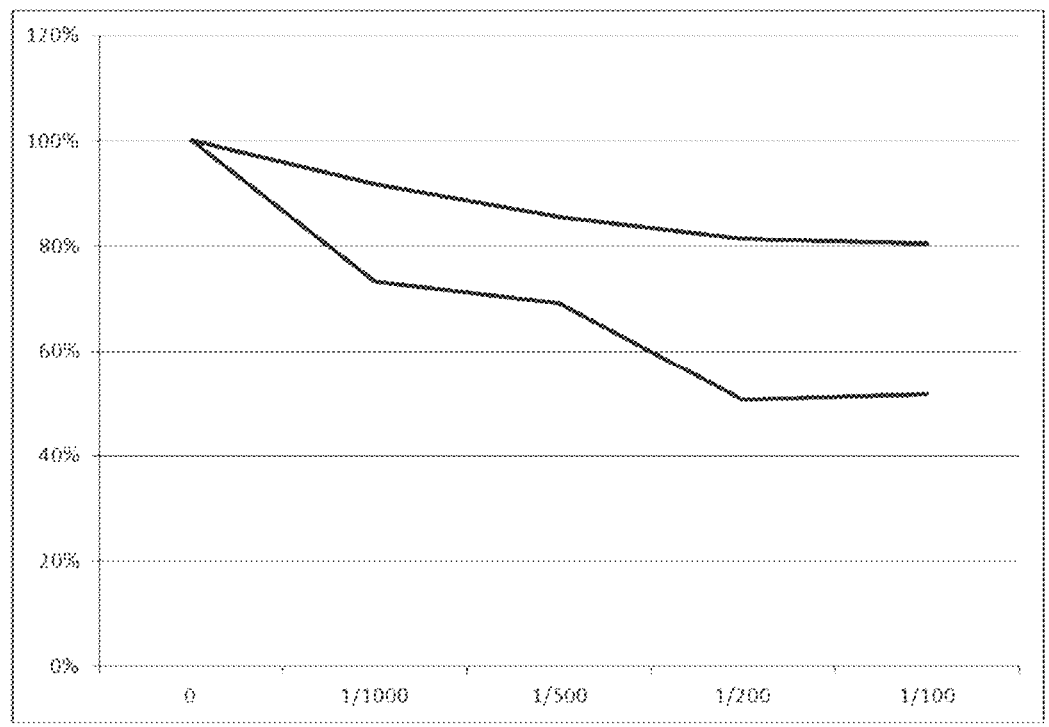

FIG. 10: Normalized intensities relative to the reference condition (without carbon particles) of the brightness level of the bottom of the well (lower curve) and the signal of the reference spot (upper curve), based on the dilution of the absorbent composition comprising the carbon particles.

Figure 11:
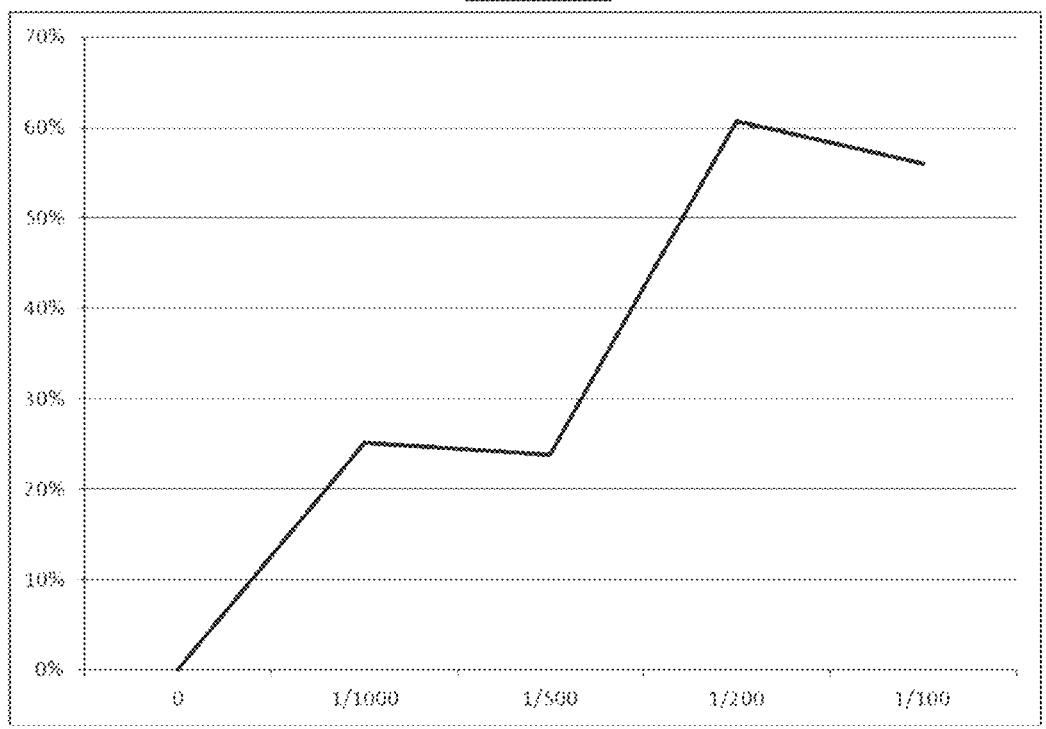

FIG. 11: Improvement of the detected signal to background noise ratio of the dilution of the absorbent composition comprising the carbon particles.

Figure 12:
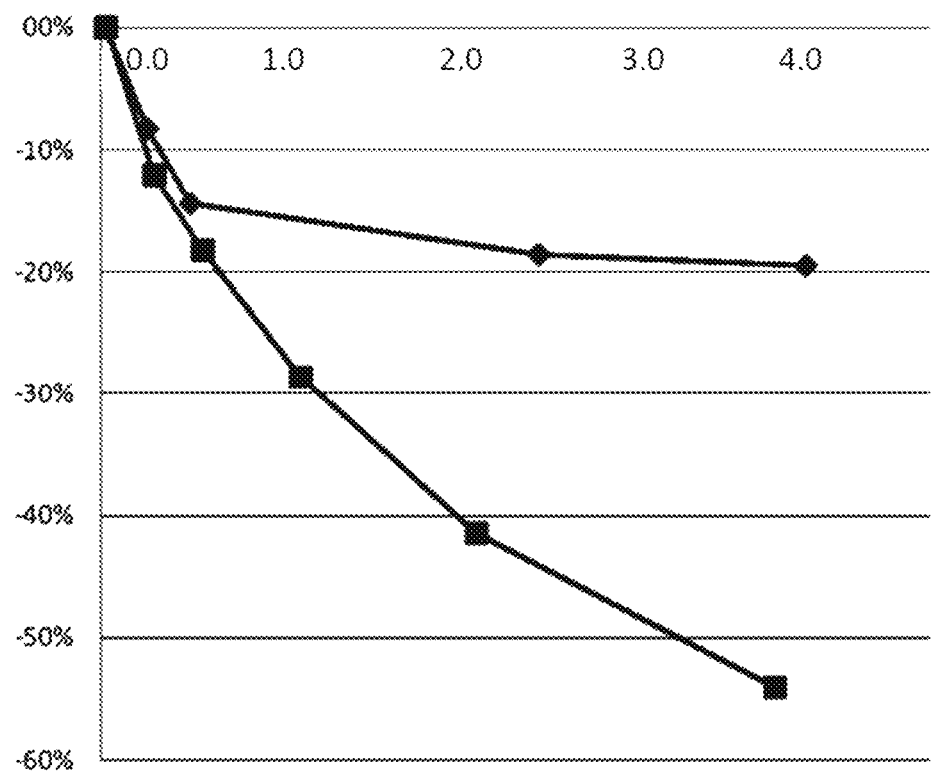

FIG. 12: Evolution of the intensity of the signal of the reference spot relative to the condition with no absorbent solution, in the case of addition of absorbent particles (upper curve) and in the case of addition of dye (lower curve), based on the optical density of the liquid phase present.

Figure 13:
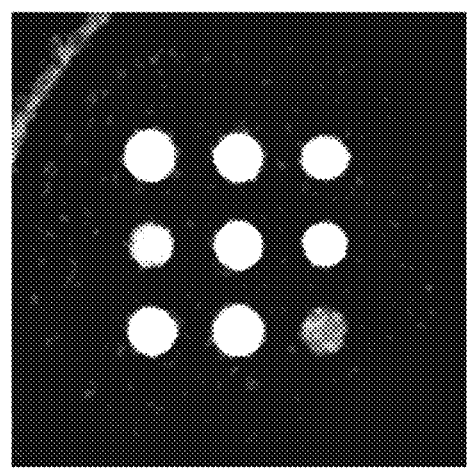

FIG. 13: Detection of spots by fluorescence in the presence of absorbent particles.

EXAMPLES

Materials and Methods

A multiplex analysis method is done using a microplate with 96 wells comprising 9 spots per well (3 spots numbered from 1 to 3 on the $1^{st}$ line, 3 spots numbered from 4 to 6 on the $2^{nd}$ line and 3 spots numbered from 7 to 9 on the $3^{rd}$ line).

Spot number 1 comprises a specific capture ligand of an analyte AH that is present in a high concentration in the reference specimen S1 used.

During the analysis method, the specimen S1 is placed in the presence of the spots of a well for 40 minutes at 37° C. After washing of the well, a specific detection ligand of the analyte or corresponding to the analyte AH present in the reference specimen S1 and coupled to the biotin is added into the well. After 15 minutes of incubation at 37° C., the well is washed and the streptavidin reporter coupled to a peroxidase enzyme is added into the well. After 15 minutes of incubation at 37° C., the well is washed. The "ELISTAR ETA C Ultra ELISA" kit (Cyanagen, Italy) is used for the developing step, according to the manufacturer's manual. It consists of contributing two solutions: a solution A that comprises the substrate of the enzyme, i.e., luminol and an electron mediator (sodium 3-(10'phenothiazinyl)propane 1-sulfonate), and a solution B that comprises an oxidizer (peroxide solution). Before acquiring the signal, a dilution of an absorbent composition comprising carbon particles is added, if applicable, into the wells. The absorbent composition can be added in mixture with solution B or solution A, with no noticeable difference in the results obtained in the two modes. The absorbent composition used in this example is the CAB-O-J ET® 352K product by Cabot (United States).

The signal emitted by chemiluminescence by the chemiluminescent product resulting from the enzymatic reaction is measured using an image taken by a CDD camera through a telecentric objective.

The brightness level of the bottom of the wells is also measured on the same image.

To measure the signal by fluorescence, a lighting system emitting a red light centered on the wavelength of 620 nm illuminates the lower face of the solid support homogenously, A filter arranged at the input of the camera and having a bandwidth centered at 680 nm makes it possible to cut this red excitation light. It allows the light emitted by the fluorophore present in the spots to pass. The signal emitted by fluorescence by the spots is measured using this device.

Results (i) Improvement of the Detection of the Signal in the Presence of Carbon Particles In the case of specimen 51, a very intense light is emitted at the spot corresponding to the analyte AH (spot number 1 in the spots grid).

Under the reference conditions (see FIG. 3), in the absence of the absorbent composition, i.e., in the absence of the dispersion of carbon particles, one can see a light ring (1) over the entire perimeter of the bottom of the well, resulting from the image of the vertical wall of the well perceived through the liquid acting as a planner-concave lens. The ring can prove extremely intense near the spot corresponding to the highly bright analyte and thus have a light arc (2). A light web is thus present over the entire bottom of the well.

In the presence of carbon particles in suspension, one can see the disappearance of the light ring over the perimeter of the well and the reduction of the light web (see FIGS. 4 to 7).

One sometimes sees, in the absence of the absorbent composition, shifted from the spots, a slightly smaller light spot, resulting from the reflection of the spot on the surface of the liquid in the background (see FIG. 8 of specimen S2). In the presence of carbon particles in suspension, one can see the disappearance of the reflection of the spot previously observed (see FIG. 9).

In the case of specimen 51, the intensity of the signal of the reference spot (spot 8 or spot Aref) and the brightness level of the bottom of the well have been measured in RLU (Relative Light Units) number (see Table 1).

The results indicated in Table 1 are from two different plates. The first plate corresponds to the 1/1000 and 1/500 dilutions, and the second corresponds to the 1/200 and 1/100 dilutions.

TABLE 1

Intensity of the signal of the reference spot and brightness level of the bottom of the well

| Plate | Dilution of the absorbent composition | Intensity of the bottom of the well (in RLU) | Intensity of the reference spot (in RLU) | Intensity of the bottom of the well (%) | Intensity of the reference spot (%) |
|---|---|---|---|---|---|
| 1 | 0 | 92 | 2635 | 100.0% | 100.0% |
|   | 1/1000 | 67 | 2418 | 72.8% | 91.8% |
|   | 1/500 | 63 | 2256 | 68.5% | 85.6% |
| 2 | 0 | 95 | 2840 | 100.0% | 100.0% |
|   | 1/200 | 48 | 2314 | 50.5% | 81.5% |
|   | 1/100 | 49 | 2287 | 51.6% | 80.5% |

One can see that the light intensities decrease when one adds more carbon particles. The interesting effect is that the brightness level of the bottom of the well decreases more quickly than the level of the signal of the reference spot (see Table 1 and FIG. 10). The brightness of the bottom of the well is considered to be undesirable, generating noise in the measurement of the signal that one seeks to quantify. One may therefore conclude that the detected signal to background noise ratio is improved by adding carbon particles in suspension.

TABLE 2

Improvement of the detected signal to background noise ratio based on the dilution of the absorbent composition

| Dilution of the absorbent composition | Intensity of the bottom of the well (in RLU) | Intensity of the reference spot (in RLU) | Ratio of the intensity of the reference spot to the intensity of the bottom of the well | Improvement of the detected signal to background noise ratio (%) |
|---|---|---|---|---|
| 0 | 92 | 2635 | 28.64 | 0.0% |
| 1/1000 | 67 | 2418 | 36.09 | 26.0% |
| 1/500 | 63 | 2256 | 35.81 | 25.0% |
| 0 | 95 | 2840 | 29.89 | 0.0% |
| 1/200 | 48 | 2314 | 48.21 | 61.3% |
| 1/100 | 49 | 2287 | 46.67 | 56.1% |

The results shown in Table 2 and FIG. 11 show the improvement of the detected signal to background noise ratio when one increases the concentration of carbon particles.

(ii) Comparison of the Performance Obtained with Carbon Particles Versus Tartrazine The optical density (OD) was studied at 450 nm (close to the maximum chemiluminescent emission) of a well containing a solution doped with tartrazine and that of a well containing a solution doped with carbon particles in suspension. The inventors have in fact shown that, surprisingly, the tartrazine also makes it possible to eliminate some or all of the light interference that occurs when acquiring a signal in liquid phase.

TABLE 3

Evolution of the reference spot based on the dilution of the absorbent particle composition

| Dilution of the absorbent particle composition | OD at 450 nm | Intensity of the bottom of the well (in RLU) | Intensity of the reference spot (in RLU) | Ratio of the intensity of the reference spot to the intensity of the bottom of the well | Improvement of the detected signal of background noise ratio (%) | Decrease of the signal of the reference spot (%) |
|---|---|---|---|---|---|---|
| 0 | 0.03 | 92 | 2635 | 28.64 | 0.0% | 0.0% |
| 1/1000 | 0.26 | 67 | 2418 | 36.09 | 26.0% | −8.2% |
| 1/500 | 0.49 | 63 | 2256 | 35.81 | 25.0% | −14.4% |
| 0 | 0.03 | 95 | 2840 | 29.89 | 0.0% | 0.0% |

TABLE 3-continued

Evolution of the reference spot based on the dilution of the absorbent particle composition

| Dilution of the absorbent particle composition | OD at 450 nm | Intensity of the bottom of the well (in RLU) | Intensity of the reference spot (in RLU) | Ratio of the intensity of the reference spot to the intensity of the bottom of the well | Improvement of the detected signal of background noise ratio (%) | Decrease of the signal of the reference spot (%) |
|---|---|---|---|---|---|---|
| 1/200 | 2.42 | 48 | 2314 | 48.21 | 61.3% | −18.5% |
| 1/100 | 3.90 | 49 | 2287 | 46.67 | 56.1% | −19.5% |

TABLE 4

Evolution of the reference spot based on the dilution of the absorbent tartrazine composition

| Tartrazine concentration (μg/ml) | OD at 450 nm | Intensity of the bottom of the well (in RLU) | Intensity of the reference spot (in RLU) | Ratio of the intensity of the reference spot to the intensity of the bottom of the well | Improvement of the signal to noise ratio (%) | Decrease of the signal of the reference spot (%) |
|---|---|---|---|---|---|---|
| 0 | 0.03 | 77 | 3168 | 41.14 | 0.0% | 0.0% |
| 250 | 0.30 | 53 | 2784 | 52.53 | 27.7% | −12.1% |
| 500 | 0.56 | 47 | 2592 | 55.15 | 34.0% | −18.2% |
| 1000 | 1.11 | 40 | 2262 | 56.55 | 37.4% | −28.6% |
| 2000 | 2.08 | 31 | 1854 | 59.81 | 45.4% | −41.5% |
| 4000 | 3.73 | 33 | 1455 | 44.09 | 7.2% | −54.1% |

The results shown in Tables 3 and 4 show that for the use of a concentration of 250 μg/ml of tartrazine, an OD of 0.3 is obtained. The equivalent is obtained with a dispersion of carbon particles diluted at 1/1000. On the reference spot, a signal loss of 8% is observed in the presence of carbon particles and 12% in the presence of tartrazine. For the use of a concentration of 4000 μg/ml of tartrazine, an OD close to 3.8 is obtained. The equivalent is obtained with a dispersion of carbon particles diluted at 1/100. On the reference spot, a signal loss of less than 20% is observed in the presence of carbon particles and more than 50% in the presence of tartrazine. The addition of carbon particles in suspension is therefore more advantageous than the tartrazine, since it influences the detected signal less, at an equal optical density of the liquid phase (see FIG. 12).

(iii) Detection of Spots by Fluorescence in the Presence of Absorbent Particles

It has also been verified that the signal emitted by a fluorophore present as control in the spots of a microplate is indeed detected in the presence of absorbent particles.

As can be seen in FIG. 13, in the presence of an absorbent solution comprising the Cab-O-Jet 352K product (1/200 dilution), the signal detected by fluorescence makes it possible to define the position of the spots very clearly relative to the bottom of the well. The addition of an absorbent solution therefore does not prevent the detection of the signal emitted by fluorescence by a fluorophore present in the spots as control.

However, the background noise obtained by fluorescence is doubled in the presence of absorbent particles relative to the background noise obtained in their absence. As a result, this detected signal to noise ratio is decreased by half.

The invention claimed is:

1. An absorbent composition comprising absorbent particles selected from the group consisting of carbon particles and color particles and at least one compound selected from the group consisting of luminol, isoluminol, a derivative of luminol or isoluminol, an electron mediator and an oxidizer, wherein said absorbent particles comprise 10% to 20% of the total weight of the absorbent composition and, optionally, said absorbent particles comprise one or more functional group.

2. A kit comprising at least two compositions:
   a first composition comprising at least one compound selected from the group consisting of luminol, isoluminol and a derivative of luminol or isoluminol, and, optionally, comprising at least one electron mediator, and
   a second composition comprising at least one oxidizer, characterized in that the first composition and/or the second composition comprises absorbent particles wherein said absorbent particles comprise 10% to 20% of the total weight of the absorbent composition and/or in that said kit comprises a third composition comprising absorbent particles wherein said absorbent particles comprise 10 to 20% of the total weight of the absorbent composition and are selected from the group consisting of carbon particles and color particles.

3. The absorbent composition according to claim 1, wherein said absorbent particles comprise 15% of the total weight of the absorbent composition.

4. The absorbent composition according to claim 1, wherein said absorbent particles comprise 12% to 18% of the total weight of the absorbent composition.

5. The absorbent composition according to claim 1, wherein the absorbent composition comprises from 12% to 18% of absorbent particles, the percentages being expressed by weight of the total weight of the absorbent composition and three or more of the following features:
   a) it comprises absorbent particles having an average diameter from 0.06 μm to 0.1 μm;
   b) it comprises absorbent particles on the surface of which one or more functional group is attached;
   c) it has a surface tension of 65 dynes/cm to 75 dynes/cm;
   d) it has a pH of 8 to 10; and/or
   e) it has a viscosity from 1 cP to 2.5 cP.

6. The absorbent composition according to claim 1, wherein the absorbent composition comprises the following features:
   a) it comprises absorbent particles having an average diameter comprised from 0.06 μm to 0.1 μm;
   b) it comprises absorbent particles on the surface of which one or more functional group is attached; and
   c) it comprises from 12% to 18% of absorbent particles, the percentages being expressed by weight of the total weight of the absorbent composition.

7. The absorbent composition according to claim 1, wherein the absorbent composition comprises absorbent particles selected from the group consisting of carbon particles and color particles; luminol, isoluminol, a derivative of luminol or a derivative of isoluminol; an electron mediator; and an oxidizer, said absorbent particles optionally comprising one or more functional group.

8. The absorbent composition according to claim 1, wherein the absorbent particles comprise one or more functional group.

9. The absorbent composition according to claim 1, wherein the absorbent composition consists of absorbent particles selected from the group consisting of carbon particles and color particles; luminol, isoluminol, a derivative of luminol or a derivative of isoluminol; an electron mediator; and an oxidizer, said absorbent particles optionally comprising one or more functional group.

10. The absorbent composition according to claim 9, wherein the absorbent particles comprise one or more functional group.

11. An analysis method comprising the following steps:
   a) providing a solid support comprising at least one compartment, said compartment comprising at least one spot for the detection of an analyte,
   b) placing a specimen to be analyzed in said compartment,
   c) placing at least one detection ligand of an analyte in said compartment, said detection ligand of an analyte being coupled to a direct or indirect detection marker,
   d) placing an absorbent composition in contact with the spot(s) of said compartment, said absorbent composition comprising absorbent particles selected from the group consisting of carbon particles and color particles and at least one compound selected from the group consisting of luminol, isoluminol, a derivative of luminol or isoluminol, an electron mediator and an oxidizer, wherein said absorbent particles comprise 10% to 20% of the total weight of the absorbent composition and, optionally, said absorbent particles comprise one or more functional group, and
   e) detecting a signal corresponding to the presence of an analyte at the spot(s) of said compartment, in the presence of the liquid phase comprising said absorbent particles.

12. The method according to claim 11, wherein the signal is detected in step e) through the bottom of the solid support.

13. The method according to claim 11, wherein the signal detected in step e) is the signal emitted by a luminescent compound and/or the signal emitted by a fluorophore.

14. The method according to claim 11, wherein said detection marker is an indirect detection marker and step c) comprises placing a reporter of the indirect detection marker coupled to said detection ligand in said compartment.

15. The method according to claim 14, wherein the reporter is coupled to an indirect marker and a reporter of the indirect detection marker coupled to said reporter is placed in said compartment.

* * * * *